(12) United States Patent
Kruljec et al.

(10) Patent No.: US 12,195,512 B2
(45) Date of Patent: Jan. 14, 2025

(54) AFFINITY LIGANDS FOR ANTIBODY Fc REGION

(71) Applicant: Univerza v Ljubljani, Ljubljana (SI)

(72) Inventors: Nika Kruljec, Moravče (SI); Tomaž Bratkovič, Ljubljana (SI); Peter Molek, Metlika (SI); Mojca Lunder, Ljubljana (SI)

(73) Assignee: Univerza v Ljubljani, Ljubljana (SI)

( * ) Notice: Subject to any disclaimer, the term of this patent is extended or adjusted under 35 U.S.C. 154(b) by 211 days.

(21) Appl. No.: 16/965,814

(22) PCT Filed: Feb. 1, 2019

(86) PCT No.: PCT/EP2019/052484
§ 371 (c)(1),
(2) Date: Jul. 29, 2020

(87) PCT Pub. No.: WO2019/149878
PCT Pub. Date: Aug. 8, 2019

(65) Prior Publication Data
US 2021/0054042 A1 Feb. 25, 2021

(30) Foreign Application Priority Data
Feb. 2, 2018 (LU) ......................... 100693

(51) Int. Cl.
| | |
|---|---|
| C07K 7/06 | (2006.01) |
| A61K 38/08 | (2019.01) |
| C07K 1/22 | (2006.01) |
| C07K 14/705 | (2006.01) |
| C07K 17/02 | (2006.01) |

(52) U.S. Cl.
CPC ........ *C07K 14/70503* (2013.01); *A61K 38/08* (2013.01); *C07K 1/22* (2013.01); *C07K 7/06* (2013.01); *C07K 17/02* (2013.01)

(58) Field of Classification Search
None
See application file for complete search history.

(56) References Cited

U.S. PATENT DOCUMENTS

| | | | |
|---|---|---|---|
| 3,155,582 A | 11/1964 | Laboratories | |
| 8,361,777 B2 | 1/2013 | Petkovic et al. | |

FOREIGN PATENT DOCUMENTS

| | | | | |
|---|---|---|---|---|
| EP | 2154150 A1 | 2/2010 | | |
| WO | WO 96/35950 A1 | 11/1996 | | |
| WO | WO-02094868 A2 | * 11/2002 | ........... | A61K 39/085 |
| WO | WO-2014080991 A1 | * 5/2014 | ........... | C12N 9/2402 |
| WO | WO 2019/122400 A1 | 6/2019 | | |

OTHER PUBLICATIONS

UniProt Accession No. M1BMN7, 5 pages (first available 2013) (Year: 2013).*
Unverified machine English language translation of WO-2014080991-A1 (2014) (Year: 2014).*
Khan Academy, "Enzymes and the active site", Khan Academy, available online at www.khanacademy.org/science/ap-biology/cellular-energetics/enzyme-structure-and-catalysis/a/enzymes-and-the-active-site, 13 pages (first available 2015) (Year: 2015).*
Ames et al., "Crystal structure and functional analysis of tetracenomycin ARO/CYC: Implications for cyclization specificity of aromatic polyketides" PNAS Apr. 8, 2008, 105(14):5349-5354.
Anonymous: "UPI000C015918" Dec. 20, 2017, Retrieved from the Internet: http://www.uniprot.org/uniparc/UPI000C015918 [Retrieved on Apr. 25, 2018].
Anonymous: UPI000BF4B0FF Dec. 20, 2017, Retrieved from the Internet: http://www.uniport.org/uniparc/UBPI0000BF40FF [Retrieved on Apr. 25, 2018].
Anonymous: UPI000C01A836 Dec. 20, 2017, Retrieved from the Internet: http://www.uniprot.org/uniparc/UPI0000CI01A836 [Retrieved on Apr. 25, 2018].
Bierman et al., "Plasmid cloning vectors for the conjugal transfer of DNA from *Escherichia coli* to *Streptomyces* spp" Gene 1992, 166:43-49.
Bilyk et al., "Chromosomal position effect influences the heterologous expression of genes and biosynthetic gene clusters in *Streptomyces albus* J1074" Microb Cell Fact (2017) 16:5, 8 pages.
Bilyk et al., "Cloning and Heterologous Expression of the Grecocycline Biosynthetic Gene Cluster" PLoS One 2016, 11(7): e0158682.
Birch et al., "Antibody production" Advanced Drug Delivery Reviews 2006, 58: 671-685.
Chiba et al., "Construction of a Pair of Practical *Nocardia-Escherichia coli* Shuttle Vectors" Jpn. J. Infect. Dis. 2007, 60:45-47.
Chon et al., "Advances in the production and downstream processing of antibodies" New Biotechnology Sep. 2011, 28(5): 458-463.
D'Iaz-S'Aez et al., "Structures of bacterial kynurenine formamidase reveal a crowded binuclear zinc catalytic site primed to generate a potent nucleophile" Biochem. J. 2014, 462: 581-589.
Delano et al., "Convergent Solutions to Binding at a Protein-Protein Interface" Science Feb. 2000, 287: 1279-1283.
Hanke et al., "Purifying biopharmaceuticals: knowledge-based chromatographic process development" Trends in Biotechnology, Apr. 2014, 32(4): 210-220.
Hautala et al., "Studies on a Second and Third Ring Cyclization in Anthracycline Biosynthesis" The Journal of Antibiotics Feb. 2003, 56(2): 143-153.

(Continued)

*Primary Examiner* — Thea D' Ambrosio
(74) *Attorney, Agent, or Firm* — Lisa Mueller; Casimir Jones SC

(57) ABSTRACT

The present invention relates to ligand that may be a peptide compound as well as peptoid or retro-inverso analogues thereof with binding affinity for the Fc region of immunoglobulins. The invention further relates to the application of such peptides and variants thereof for purification of immunoglobulins on the basis of affinity chromatography, non-covalent antibody labelling, antibody detection or immobilization of antibodies to solid support.

Figure 1:
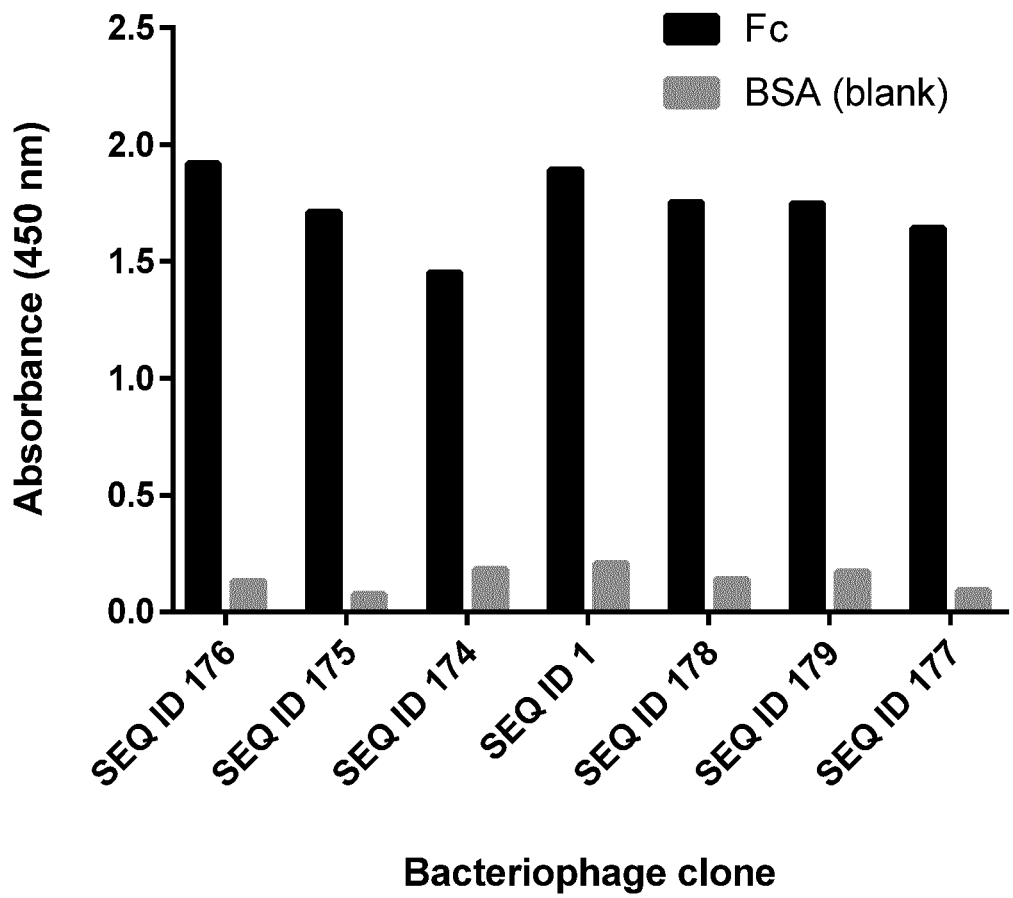

2 Claims, 15 Drawing Sheets
Specification includes a Sequence Listing.

(56) References Cited

OTHER PUBLICATIONS

Hopwood & Sherman, "Molecular genetics of polyketides and its comparison to fatty biosynthesis" Annu. Rev. Genet. 1990, 24:37-66.

Jungbauer et al., "Continuous downstream processing of biopharmaceuticals" Trends in Biotechnology, Aug. 2013, 31(8): 479-492.

Koguma et al., "Novel purification method of human immunoglobulin by using a thermo-responsive protein A" Journal of Chromatography A, 2013, 1305: 149-153.

Koshla et al., "Properties of *Streptomyces albus* J1074 mutant deficient in tRNA$^{Leu}$UAA gene bldA" Arch Microbiol 2017, 199:1175-1183.

Kruljec et al., "Alternative Affinity Ligands for Immunoglobulins" Bioconjug Chem. Aug. 16, 2017; 28(8):2009-2030.

Lebrou, "Design and selection of ligands for affinity chromatography" Journal of Chromatography B 2003, 790: 67-78.

Lešnik et al., "Construction of a New Class of Tetracycline Lead Structures with Potent Antibacterial Activity through Biosynthetic Engineering" Angew. Chem. 2015, 127:4009-4012.

Lešnik et al., "Regulatory Elements in Tetracycline-Encoding Gene Clusters: the otcG Gene Positively Regulates the Production of Oxytetracycline in Streptomyces rimosus" Food Technol. Biotechnol. 2009, 47(3):323-330.

Li et al., "Cell culture processes for monoclonal antibody production" mAbs Sep./Oct. 2010; 2(5): 466-477.

Li et al., "Design, synthesis, and application of a Protein A mimetic" Nature Biotechnology 1998, 16: 190-195.

LU Search Report and Written Opinion for LU Appl. No. LU100693, dated Nov. 6, 2018, 8 pages.

Lukežičo et al., "Engineering Atypical Tetracycline Formation in Amycolatopsis sulphurea for the Production of Modified Chelocardin Antibiotics" ACS Chem. Biol. 2019, 14:468-477.

Lukežičo et al., "Identification of the chelocardin biosynthetic gene cluster from Amycolatopsis sulphurea: a platform for producing novel tetracycline antibiotics" Microbiology 2013, 159: 2524-2532.

MacNeil et al., "Analysis of Streptomyces avermitilis genes required for avermectin biosynthesis utilizing a novel integration vector" Gene 1992, 111: 61-68.

Madon & Hütter, "Transformation System for *Amycolatopsis* (*Nocardia*) medditerranei: Direct Transformation of Mycelium with Plasmid DNA" Journal of Bacteriology Oct. 1991, 173(20): 6325-6331.

Martin & McMillan, "SAM (dependent) I Am: the S-adenosylmethionine-dependent methyltransferase fold" Current Opinion in Structural Biology 2002, 12:783-793.

Mason & Cammack, "The Electron-Transport Proteins of Hydroxylating Bacterial Dioxygenases" Annu. Rev. Microbiol. 1992, 46:277-305.

Menendez et al., "Biosynthesis of the Antitumor Chromomycin A$_3$ in Streptomyces griseus: Analysis of the Gene Cluster and Rational Design of Novel Chromomycin Analogs" Chemistry & Biology Jan. 2004, 11:21-32.

Mitscher et al., "Biosynthesis of Cetocycline" The Journal of Antibiotics 1983, vol. XXXVI No. 10, 1405-1407.

Molnar et al., "clinico-pharmacological investigation of chelocardine in patients suffering from urinary tract infection" Lij. Vjes. 1977, 99:560.

Myronovskyi et al., "Generation of a cluster-free *Streptomyces albus* chassis strains for improved heterologous expression of secondary metabolite clusters" Metabolic Engineering 2018, 49: 316-324.

Nilsson et al., "A synthetic IgG-binding domain based on staphylococcal protein A" Protein Engineering 1987, 1(2): 107-113.

Paget et al., "Evidence that the Extracytoplasmic Function Sigma Factor σ$^{69}$ Is Required for Normal Cell Wall Structure in *Streptomyces coelicolor* A3(2)." Journal of Bacteriology, Jan. 1999, p. 204-211.

Pickens & Tang, "Oxytetracycline Biosynthesis" The Journal of Biological Chemistry, Sep. 3, 2010, 285(36): 27509-27515.

Proctor et al., "Cetocycline, Tetracycline Analog: In Vitro Studies of Antimicrobial Activity, Serum Binding, Lipid Solubility, and Uptake by Bacteria" Antimicrobial Agents and Chemotherapy, Apr. 1978, 13(4): 598-604.

Rasmussen et al., "Molecular Basis of Tetracycline Action: Identification of Analogs Whose Primary Target Is Not the Bacterial Ribosome" Antimicrobial Agents and Chemotherapy, Nov. 1991, 35(11): 2306-2311.

Rawlings et al., "The Gene Encoding *Escherichia coli* Acyl Carrier Protein Lies within a Cluster of Fatty Acid Biosynthetic Genes" The Journal of Biological Chemistry, Mar. 1992, 267(9): 5751-5754.

Revill et al., "Purification of a Malonyltransferase from *Streptomyces coelicolor* A3(2) and Analysis of Its Genetic Determinant" Journal of Bacteriology, Jul. 1995, 177(14):3946-3952.

Roque et al., "Affinity-based methodologies and ligands for antibody purification: Advances and perspectives" Journal of Chromatography A 2007, 1160: 44-55.

Shukla & Thommes, "Recent advances in large-scale production of monoclonal antibodies and related proteins" Trends in Biotechnology 2010, 28(5): 253-261.

Sidorin et al., "IgG Binding Proteins of Bacteria" Biochemistry (Moscow), 2011, 76(3): 295-308.

Yang et al., "Purification of human immunoglobulin G via Fc-specific small peptide ligand affinity chromatography" Journal of Chromatography A 2009, 1216: 910-918.

\* cited by examiner

SEQUENCE LISTING

```
<160> NUMBER OF SEQ ID NOS: 218

<210> SEQ ID NO 1
<211> LENGTH: 12
<212> TYPE: PRT
<213> ORGANISM: Artificial Sequence
<220> FEATURE:
<223> OTHER INFORMATION: Immunoglobulin binding ligand

<400> SEQUENCE: 1

Ala Gly Asn Gly Ser Tyr Trp Tyr Gln Val Trp Phe
1               5                   10

<210> SEQ ID NO 2
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 2

Gly Ser Tyr Trp Tyr Gln Val Trp Phe
1               5

<210> SEQ ID NO 3
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 3

Ser Tyr Trp Tyr Gln Val Trp Phe
1               5

<210> SEQ ID NO 4
<211> LENGTH: 8
<212> TYPE: PRT
<213> ORGANISM: Artificial Sequence
<220> FEATURE:
<223> OTHER INFORMATION: Immunoglobulin binding ligand
```

-continued

```
<400> SEQUENCE: 4

Gly Tyr Trp Tyr Gln Val Trp Phe
1               5

<210> SEQ ID NO 5
<211> LENGTH: 7
<212> TYPE: PRT
<213> ORGANISM: Artificial Sequence
<220> FEATURE:
<223> OTHER INFORMATION: Immunoglobulin binding ligand

<400> SEQUENCE: 5

Tyr Trp Tyr Gln Val Trp Phe
1               5

<210> SEQ ID NO 6
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 6

Gly Ser Tyr Trp Tyr Ala Val Trp Phe
1               5

<210> SEQ ID NO 7
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 7

Ser Tyr Trp Tyr Ala Val Trp Phe
1               5

<210> SEQ ID NO 8
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 8

Gly Tyr Trp Tyr Ala Val Trp Phe
1               5

<210> SEQ ID NO 9
<211> LENGTH: 7
<212> TYPE: PRT
<213> ORGANISM: Artificial Sequence
<220> FEATURE:
<223> OTHER INFORMATION: Immunoglobulin binding ligand

<400> SEQUENCE: 9

Tyr Trp Tyr Ala Val Trp Phe
1               5

<210> SEQ ID NO 10
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 10
```

```
Gly Ser Tyr Trp Tyr Gln Ala Trp Phe
1               5

<210> SEQ ID NO 11
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 11

Ser Tyr Trp Tyr Gln Ala Trp Phe
1               5

<210> SEQ ID NO 12
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 12

Gly Tyr Trp Tyr Gln Ala Trp Phe
1               5

<210> SEQ ID NO 13
<211> LENGTH: 7
<212> TYPE: PRT
<213> ORGANISM: Artificial Sequence
<220> FEATURE:
<223> OTHER INFORMATION: Immunoglobulin binding ligand

<400> SEQUENCE: 13

Tyr Trp Tyr Gln Ala Trp Phe
1               5

<210> SEQ ID NO 14
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 14

Gly Asn Tyr Trp Tyr Gln Val Trp Phe
1               5

<210> SEQ ID NO 15
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 15

Asn Tyr Trp Tyr Gln Val Trp Phe
1               5

<210> SEQ ID NO 16
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 16
```

```
Gly Thr Tyr Trp Tyr Gln Val Trp Phe
1               5

<210> SEQ ID NO 17
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 17

Thr Tyr Trp Tyr Gln Val Trp Phe
1               5

<210> SEQ ID NO 18
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 18

Gly Lys Tyr Trp Tyr Gln Val Trp Phe
1               5

<210> SEQ ID NO 19
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 19

Lys Tyr Trp Tyr Gln Val Trp Phe
1               5

<210> SEQ ID NO 20
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 20

Gly Cys Tyr Trp Tyr Gln Val Trp Phe
1               5

<210> SEQ ID NO 21
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 21

Cys Tyr Trp Tyr Gln Val Trp Phe
1               5

<210> SEQ ID NO 22
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 22

Gly Ser Tyr Trp Tyr Gln Lys Trp Phe
```

```
<210> SEQ ID NO 23
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 23

Ser Tyr Trp Tyr Gln Lys Trp Phe
1               5

<210> SEQ ID NO 24
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 24

Gly Tyr Trp Tyr Gln Lys Trp Phe
1               5

<210> SEQ ID NO 25
<211> LENGTH: 7
<212> TYPE: PRT
<213> ORGANISM: Artificial Sequence
<220> FEATURE:
<223> OTHER INFORMATION: Immunoglobulin binding ligand

<400> SEQUENCE: 25

Tyr Trp Tyr Gln Lys Trp Phe
1               5

<210> SEQ ID NO 26
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 26

Gly Ser Tyr Trp Tyr Asp Val Trp Phe
1               5

<210> SEQ ID NO 27
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 27

Ser Tyr Trp Tyr Asp Val Trp Phe
1               5

<210> SEQ ID NO 28
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 28

Gly Tyr Trp Tyr Asp Val Trp Phe
1               5
```

```
<210> SEQ ID NO 29
<211> LENGTH: 7
<212> TYPE: PRT
<213> ORGANISM: Artificial Sequence
<220> FEATURE:
<223> OTHER INFORMATION: Immunoglobulin binding ligand

<400> SEQUENCE: 29

Tyr Trp Tyr Asp Val Trp Phe
1               5

<210> SEQ ID NO 30
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 30

Gly Ser Tyr Trp Tyr Glu Val Trp Phe
1               5

<210> SEQ ID NO 31
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 31

Ser Tyr Trp Tyr Glu Val Trp Phe
1               5

<210> SEQ ID NO 32
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 32

Gly Tyr Trp Tyr Glu Val Trp Phe
1               5

<210> SEQ ID NO 33
<211> LENGTH: 7
<212> TYPE: PRT
<213> ORGANISM: Artificial Sequence
<220> FEATURE:
<223> OTHER INFORMATION: Immunoglobulin binding ligand

<400> SEQUENCE: 33

Tyr Trp Tyr Glu Val Trp Phe
1               5

<210> SEQ ID NO 34
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 34

Gly Ser Tyr Trp Tyr Lys Val Trp Phe
1               5
```

```
<210> SEQ ID NO 35
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 35

Ser Tyr Trp Tyr Lys Val Trp Phe
1               5

<210> SEQ ID NO 36
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 36

Gly Tyr Trp Tyr Lys Val Trp Phe
1               5

<210> SEQ ID NO 37
<211> LENGTH: 7
<212> TYPE: PRT
<213> ORGANISM: Artificial Sequence
<220> FEATURE:
<223> OTHER INFORMATION: Immunoglobulin binding ligand

<400> SEQUENCE: 37

Tyr Trp Tyr Lys Val Trp Phe
1               5

<210> SEQ ID NO 38
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 38

Gly Ser Tyr Trp Tyr Ala Ala Trp Phe
1               5

<210> SEQ ID NO 39
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 39

Gly Ser Tyr Trp Tyr Ala Lys Trp Phe
1               5

<210> SEQ ID NO 40
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 40

Gly Ser Tyr Trp Tyr Asp Ala Trp Phe
1               5
```

```
<210> SEQ ID NO 41
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 41

Gly Ser Tyr Trp Tyr Asp Lys Trp Phe
1               5

<210> SEQ ID NO 42
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 42

Gly Ser Tyr Trp Tyr Glu Ala Trp Phe
1               5

<210> SEQ ID NO 43
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 43

Gly Ser Tyr Trp Tyr Glu Lys Trp Phe
1               5

<210> SEQ ID NO 44
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 44

Gly Ser Tyr Trp Tyr Lys Ala Trp Phe
1               5

<210> SEQ ID NO 45
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 45

Gly Ser Tyr Trp Tyr Lys Lys Trp Phe
1               5

<210> SEQ ID NO 46
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 46

Ser Tyr Trp Tyr Ala Ala Trp Phe
1               5

<210> SEQ ID NO 47
```

```
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 47

Ser Tyr Trp Tyr Ala Lys Trp Phe
1               5

<210> SEQ ID NO 48
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 48

Ser Tyr Trp Tyr Asp Ala Trp Phe
1               5

<210> SEQ ID NO 49
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 49

Ser Tyr Trp Tyr Asp Lys Trp Phe
1               5

<210> SEQ ID NO 50
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 50

Ser Tyr Trp Tyr Glu Ala Trp Phe
1               5

<210> SEQ ID NO 51
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 51

Ser Tyr Trp Tyr Glu Lys Trp Phe
1               5

<210> SEQ ID NO 52
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 52

Ser Tyr Trp Tyr Lys Ala Trp Phe
1               5

<210> SEQ ID NO 53
<211> LENGTH: 8
```

```
<212> TYPE: PRT
<213> ORGANISM: Artificial Sequence
<220> FEATURE:
<223> OTHER INFORMATION: Immunoglobulin binding ligand

<400> SEQUENCE: 53

Ser Tyr Trp Tyr Lys Lys Trp Phe
1               5

<210> SEQ ID NO 54
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 54

Gly Thr Tyr Trp Tyr Ala Val Trp Phe
1               5

<210> SEQ ID NO 55
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 55

Gly Thr Tyr Trp Tyr Gln Ala Trp Phe
1               5

<210> SEQ ID NO 56
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 56

Gly Thr Tyr Trp Tyr Ala Ala Trp Phe
1               5

<210> SEQ ID NO 57
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 57

Gly Thr Tyr Trp Tyr Ala Lys Trp Phe
1               5

<210> SEQ ID NO 58
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 58

Gly Thr Tyr Trp Tyr Asp Val Trp Phe
1               5

<210> SEQ ID NO 59
<211> LENGTH: 9
<212> TYPE: PRT
```

<213> ORGANISM: Artificial Sequence
<220> FEATURE:
<223> OTHER INFORMATION: Immunoglobulin binding ligand

<400> SEQUENCE: 59

Gly Thr Tyr Trp Tyr Asp Ala Trp Phe
1               5

<210> SEQ ID NO 60
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 60

Gly Thr Tyr Trp Tyr Asp Lys Trp Phe
1               5

<210> SEQ ID NO 61
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 61

Gly Thr Tyr Trp Tyr Glu Val Trp Phe
1               5

<210> SEQ ID NO 62
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 62

Gly Thr Tyr Trp Tyr Glu Ala Trp Phe
1               5

<210> SEQ ID NO 63
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 63

Gly Thr Tyr Trp Tyr Glu Lys Trp Phe
1               5

<210> SEQ ID NO 64
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 64

Gly Thr Tyr Trp Tyr Lys Val Trp Phe
1               5

<210> SEQ ID NO 65
<211> LENGTH: 9
<212> TYPE: PRT
<213> ORGANISM: Artificial Sequence

```
<220> FEATURE:
<223> OTHER INFORMATION: Immunoglobulin binding ligand

<400> SEQUENCE: 65

Gly Thr Tyr Trp Tyr Lys Ala Trp Phe
1               5

<210> SEQ ID NO 66
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 66

Gly Thr Tyr Trp Tyr Lys Lys Trp Phe
1               5

<210> SEQ ID NO 67
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 67

Gly Thr Tyr Trp Tyr Gln Lys Trp Phe
1               5

<210> SEQ ID NO 68
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 68

Thr Tyr Trp Tyr Ala Val Trp Phe
1               5

<210> SEQ ID NO 69
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 69

Thr Tyr Trp Tyr Gln Ala Trp Phe
1               5

<210> SEQ ID NO 70
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 70

Thr Tyr Trp Tyr Ala Ala Trp Phe
1               5

<210> SEQ ID NO 71
<211> LENGTH: 8
<212> TYPE: PRT
<213> ORGANISM: Artificial Sequence
<220> FEATURE:
```

```
<223> OTHER INFORMATION: Immunoglobulin binding ligand

<400> SEQUENCE: 71

Thr Tyr Trp Tyr Ala Lys Trp Phe
1               5

<210> SEQ ID NO 72
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 72

Thr Tyr Trp Tyr Asp Val Trp Phe
1               5

<210> SEQ ID NO 73
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 73

Thr Tyr Trp Tyr Asp Ala Trp Phe
1               5

<210> SEQ ID NO 74
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 74

Thr Tyr Trp Tyr Asp Lys Trp Phe
1               5

<210> SEQ ID NO 75
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 75

Thr Tyr Trp Tyr Glu Val Trp Phe
1               5

<210> SEQ ID NO 76
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 76

Thr Tyr Trp Tyr Glu Ala Trp Phe
1               5

<210> SEQ ID NO 77
<211> LENGTH: 8
<212> TYPE: PRT
<213> ORGANISM: Artificial Sequence
<220> FEATURE:
<223> OTHER INFORMATION: Immunoglobulin binding ligand
```

<400> SEQUENCE: 77

Thr Tyr Trp Tyr Glu Lys Trp Phe
1               5

<210> SEQ ID NO 78
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 78

Thr Tyr Trp Tyr Lys Val Trp Phe
1               5

<210> SEQ ID NO 79
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 79

Thr Tyr Trp Tyr Lys Ala Trp Phe
1               5

<210> SEQ ID NO 80
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 80

Thr Tyr Trp Tyr Lys Lys Trp Phe
1               5

<210> SEQ ID NO 81
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 81

Thr Tyr Trp Tyr Gln Lys Trp Phe
1               5

<210> SEQ ID NO 82
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 82

Gly Asn Tyr Trp Tyr Ala Val Trp Phe
1               5

<210> SEQ ID NO 83
<211> LENGTH: 9
<212> TYPE: PRT
<213> ORGANISM: Artificial Sequence
<220> FEATURE:
<223> OTHER INFORMATION: Immunoglobulin binding ligand

```
<400> SEQUENCE: 83

Gly Asn Tyr Trp Tyr Gln Ala Trp Phe
1               5

<210> SEQ ID NO 84
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 84

Gly Asn Tyr Trp Tyr Ala Ala Trp Phe
1               5

<210> SEQ ID NO 85
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 85

Gly Asn Tyr Trp Tyr Ala Lys Trp Phe
1               5

<210> SEQ ID NO 86
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 86

Gly Asn Tyr Trp Tyr Asp Val Trp Phe
1               5

<210> SEQ ID NO 87
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 87

Gly Asn Tyr Trp Tyr Asp Ala Trp Phe
1               5

<210> SEQ ID NO 88
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 88

Gly Asn Tyr Trp Tyr Asp Lys Trp Phe
1               5

<210> SEQ ID NO 89
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 89
```

Gly Asn Tyr Trp Tyr Glu Val Trp Phe
1               5

<210> SEQ ID NO 90
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 90

Gly Asn Tyr Trp Tyr Glu Ala Trp Phe
1               5

<210> SEQ ID NO 91
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 91

Gly Asn Tyr Trp Tyr Glu Lys Trp Phe
1               5

<210> SEQ ID NO 92
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 92

Gly Asn Tyr Trp Tyr Lys Val Trp Phe
1               5

<210> SEQ ID NO 93
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 93

Gly Asn Tyr Trp Tyr Lys Ala Trp Phe
1               5

<210> SEQ ID NO 94
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 94

Gly Asn Tyr Trp Tyr Lys Lys Trp Phe
1               5

<210> SEQ ID NO 95
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 95

-continued

```
Gly Asn Tyr Trp Tyr Gln Lys Trp Phe
1               5

<210> SEQ ID NO 96
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 96

Asn Tyr Trp Tyr Ala Val Trp Phe
1               5

<210> SEQ ID NO 97
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 97

Asn Tyr Trp Tyr Gln Ala Trp Phe
1               5

<210> SEQ ID NO 98
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 98

Asn Tyr Trp Tyr Ala Ala Trp Phe
1               5

<210> SEQ ID NO 99
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 99

Asn Tyr Trp Tyr Ala Lys Trp Phe
1               5

<210> SEQ ID NO 100
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 100

Asn Tyr Trp Tyr Asp Val Trp Phe
1               5

<210> SEQ ID NO 101
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 101

Asn Tyr Trp Tyr Asp Ala Trp Phe
```

```
1               5
```

<210> SEQ ID NO 102
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 102

```
Asn Tyr Trp Tyr Asp Lys Trp Phe
1               5
```

<210> SEQ ID NO 103
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 103

```
Asn Tyr Trp Tyr Glu Val Trp Phe
1               5
```

<210> SEQ ID NO 104
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 104

```
Asn Tyr Trp Tyr Glu Ala Trp Phe
1               5
```

<210> SEQ ID NO 105
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 105

```
Asn Tyr Trp Tyr Glu Lys Trp Phe
1               5
```

<210> SEQ ID NO 106
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 106

```
Asn Tyr Trp Tyr Lys Val Trp Phe
1               5
```

<210> SEQ ID NO 107
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 107

```
Asn Tyr Trp Tyr Lys Ala Trp Phe
1               5
```

```
<210> SEQ ID NO 108
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 108

Asn Tyr Trp Tyr Lys Lys Trp Phe
1               5

<210> SEQ ID NO 109
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 109

Asn Tyr Trp Tyr Gln Lys Trp Phe
1               5

<210> SEQ ID NO 110
<211> LENGTH: 7
<212> TYPE: PRT
<213> ORGANISM: Artificial Sequence
<220> FEATURE:
<223> OTHER INFORMATION: Immunoglobulin binding ligand

<400> SEQUENCE: 110

Tyr Trp Tyr Ala Ala Trp Phe
1               5

<210> SEQ ID NO 111
<211> LENGTH: 7
<212> TYPE: PRT
<213> ORGANISM: Artificial Sequence
<220> FEATURE:
<223> OTHER INFORMATION: Immunoglobulin binding ligand

<400> SEQUENCE: 111

Tyr Trp Tyr Ala Lys Trp Phe
1               5

<210> SEQ ID NO 112
<211> LENGTH: 7
<212> TYPE: PRT
<213> ORGANISM: Artificial Sequence
<220> FEATURE:
<223> OTHER INFORMATION: Immunoglobulin binding ligand

<400> SEQUENCE: 112

Tyr Trp Tyr Asp Ala Trp Phe
1               5

<210> SEQ ID NO 113
<211> LENGTH: 7
<212> TYPE: PRT
<213> ORGANISM: Artificial Sequence
<220> FEATURE:
<223> OTHER INFORMATION: Immunoglobulin binding ligand

<400> SEQUENCE: 113

Tyr Trp Tyr Asp Lys Trp Phe
1               5
```

<210> SEQ ID NO 114
<211> LENGTH: 7
<212> TYPE: PRT
<213> ORGANISM: Artificial Sequence
<220> FEATURE:
<223> OTHER INFORMATION: Immunoglobulin binding ligand

<400> SEQUENCE: 114

Tyr Trp Tyr Glu Ala Trp Phe
1               5

<210> SEQ ID NO 115
<211> LENGTH: 7
<212> TYPE: PRT
<213> ORGANISM: Artificial Sequence
<220> FEATURE:
<223> OTHER INFORMATION: Immunoglobulin binding ligand

<400> SEQUENCE: 115

Tyr Trp Tyr Glu Lys Trp Phe
1               5

<210> SEQ ID NO 116
<211> LENGTH: 7
<212> TYPE: PRT
<213> ORGANISM: Artificial Sequence
<220> FEATURE:
<223> OTHER INFORMATION: Immunoglobulin binding ligand

<400> SEQUENCE: 116

Tyr Trp Tyr Lys Ala Trp Phe
1               5

<210> SEQ ID NO 117
<211> LENGTH: 7
<212> TYPE: PRT
<213> ORGANISM: Artificial Sequence
<220> FEATURE:
<223> OTHER INFORMATION: Immunoglobulin binding ligand

<400> SEQUENCE: 117

Tyr Trp Tyr Lys Lys Trp Phe
1               5

<210> SEQ ID NO 118
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 118

Gly Cys Tyr Trp Tyr Ala Val Trp Phe
1               5

<210> SEQ ID NO 119
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 119

Gly Cys Tyr Trp Tyr Gln Ala Trp Phe
1               5

```
<210> SEQ ID NO 120
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 120

Gly Cys Tyr Trp Tyr Ala Ala Trp Phe
1               5

<210> SEQ ID NO 121
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 121

Gly Cys Tyr Trp Tyr Ala Lys Trp Phe
1               5

<210> SEQ ID NO 122
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 122

Gly Cys Tyr Trp Tyr Asp Val Trp Phe
1               5

<210> SEQ ID NO 123
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 123

Gly Cys Tyr Trp Tyr Asp Ala Trp Phe
1               5

<210> SEQ ID NO 124
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 124

Gly Cys Tyr Trp Tyr Asp Lys Trp Phe
1               5

<210> SEQ ID NO 125
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 125

Gly Cys Tyr Trp Tyr Glu Val Trp Phe
1               5

<210> SEQ ID NO 126
```

```
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 126

Gly Cys Tyr Trp Tyr Glu Ala Trp Phe
1               5

<210> SEQ ID NO 127
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 127

Gly Cys Tyr Trp Tyr Glu Lys Trp Phe
1               5

<210> SEQ ID NO 128
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 128

Gly Cys Tyr Trp Tyr Lys Val Trp Phe
1               5

<210> SEQ ID NO 129
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 129

Gly Cys Tyr Trp Tyr Lys Ala Trp Phe
1               5

<210> SEQ ID NO 130
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 130

Gly Cys Tyr Trp Tyr Lys Lys Trp Phe
1               5

<210> SEQ ID NO 131
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 131

Gly Cys Tyr Trp Tyr Gln Lys Trp Phe
1               5

<210> SEQ ID NO 132
<211> LENGTH: 8
```

```
<212> TYPE: PRT
<213> ORGANISM: Artificial Sequence
<220> FEATURE:
<223> OTHER INFORMATION: Immunoglobulin binding ligand

<400> SEQUENCE: 132

Cys Tyr Trp Tyr Ala Val Trp Phe
1               5

<210> SEQ ID NO 133
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 133

Cys Tyr Trp Tyr Gln Ala Trp Phe
1               5

<210> SEQ ID NO 134
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 134

Cys Tyr Trp Tyr Ala Ala Trp Phe
1               5

<210> SEQ ID NO 135
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 135

Cys Tyr Trp Tyr Ala Lys Trp Phe
1               5

<210> SEQ ID NO 136
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 136

Cys Tyr Trp Tyr Asp Val Trp Phe
1               5

<210> SEQ ID NO 137
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 137

Cys Tyr Trp Tyr Asp Ala Trp Phe
1               5

<210> SEQ ID NO 138
<211> LENGTH: 8
<212> TYPE: PRT
```

```
<213> ORGANISM: Artificial Sequence
<220> FEATURE:
<223> OTHER INFORMATION: Immunoglobulin binding ligand

<400> SEQUENCE: 138

Cys Tyr Trp Tyr Asp Lys Trp Phe
1               5

<210> SEQ ID NO 139
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 139

Cys Tyr Trp Tyr Glu Val Trp Phe
1               5

<210> SEQ ID NO 140
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 140

Cys Tyr Trp Tyr Glu Ala Trp Phe
1               5

<210> SEQ ID NO 141
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 141

Cys Tyr Trp Tyr Glu Lys Trp Phe
1               5

<210> SEQ ID NO 142
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 142

Cys Tyr Trp Tyr Lys Val Trp Phe
1               5

<210> SEQ ID NO 143
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 143

Cys Tyr Trp Tyr Lys Ala Trp Phe
1               5

<210> SEQ ID NO 144
<211> LENGTH: 8
<212> TYPE: PRT
<213> ORGANISM: Artificial Sequence
```

```
<220> FEATURE:
<223> OTHER INFORMATION: Immunoglobulin binding ligand

<400> SEQUENCE: 144

Cys Tyr Trp Tyr Lys Lys Trp Phe
1               5

<210> SEQ ID NO 145
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 145

Cys Tyr Trp Tyr Gln Lys Trp Phe
1               5

<210> SEQ ID NO 146
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 146

Gly Lys Tyr Trp Tyr Ala Val Trp Phe
1               5

<210> SEQ ID NO 147
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 147

Gly Lys Tyr Trp Tyr Gln Ala Trp Phe
1               5

<210> SEQ ID NO 148
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 148

Gly Lys Tyr Trp Tyr Ala Ala Trp Phe
1               5

<210> SEQ ID NO 149
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 149

Gly Lys Tyr Trp Tyr Ala Lys Trp Phe
1               5

<210> SEQ ID NO 150
<211> LENGTH: 9
<212> TYPE: PRT
<213> ORGANISM: Artificial Sequence
<220> FEATURE:
```

```
<223> OTHER INFORMATION: Immunoglobulin binding ligand

<400> SEQUENCE: 150

Gly Lys Tyr Trp Tyr Asp Val Trp Phe
1               5

<210> SEQ ID NO 151
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 151

Gly Lys Tyr Trp Tyr Asp Ala Trp Phe
1               5

<210> SEQ ID NO 152
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 152

Gly Lys Tyr Trp Tyr Asp Lys Trp Phe
1               5

<210> SEQ ID NO 153
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 153

Gly Lys Tyr Trp Tyr Glu Val Trp Phe
1               5

<210> SEQ ID NO 154
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 154

Gly Lys Tyr Trp Tyr Glu Ala Trp Phe
1               5

<210> SEQ ID NO 155
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 155

Gly Lys Tyr Trp Tyr Glu Lys Trp Phe
1               5

<210> SEQ ID NO 156
<211> LENGTH: 9
<212> TYPE: PRT
<213> ORGANISM: Artificial Sequence
<220> FEATURE:
<223> OTHER INFORMATION: Immunoglobulin binding ligand
```

<400> SEQUENCE: 156

Gly Lys Tyr Trp Tyr Lys Val Trp Phe
1               5

<210> SEQ ID NO 157
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 157

Gly Lys Tyr Trp Tyr Lys Ala Trp Phe
1               5

<210> SEQ ID NO 158
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 158

Gly Lys Tyr Trp Tyr Lys Lys Trp Phe
1               5

<210> SEQ ID NO 159
<211> LENGTH: 9
<212> TYPE: PRT
<213> ORGANISM: Artificial Sequence
<220> FEATURE:
<223> OTHER INFORMATION: Immunoglobulin binding ligand

<400> SEQUENCE: 159

Gly Lys Tyr Trp Tyr Gln Lys Trp Phe
1               5

<210> SEQ ID NO 160
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 160

Lys Tyr Trp Tyr Ala Val Trp Phe
1               5

<210> SEQ ID NO 161
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 161

Lys Tyr Trp Tyr Gln Ala Trp Phe
1               5

<210> SEQ ID NO 162
<211> LENGTH: 8
<212> TYPE: PRT
<213> ORGANISM: Artificial Sequence
<220> FEATURE:
<223> OTHER INFORMATION: Immunoglobulin binding ligand

```
<400> SEQUENCE: 162

Lys Tyr Trp Tyr Ala Ala Trp Phe
1               5

<210> SEQ ID NO 163
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 163

Lys Tyr Trp Tyr Ala Lys Trp Phe
1               5

<210> SEQ ID NO 164
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 164

Lys Tyr Trp Tyr Asp Val Trp Phe
1               5

<210> SEQ ID NO 165
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 165

Lys Tyr Trp Tyr Asp Ala Trp Phe
1               5

<210> SEQ ID NO 166
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 166

Lys Tyr Trp Tyr Asp Lys Trp Phe
1               5

<210> SEQ ID NO 167
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 167

Lys Tyr Trp Tyr Glu Val Trp Phe
1               5

<210> SEQ ID NO 168
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 168
```

```
Lys Tyr Trp Tyr Glu Ala Trp Phe
1               5

<210> SEQ ID NO 169
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 169

Lys Tyr Trp Tyr Glu Lys Trp Phe
1               5

<210> SEQ ID NO 170
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 170

Lys Tyr Trp Tyr Lys Val Trp Phe
1               5

<210> SEQ ID NO 171
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 171

Lys Tyr Trp Tyr Lys Ala Trp Phe
1               5

<210> SEQ ID NO 172
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 172

Lys Tyr Trp Tyr Lys Lys Trp Phe
1               5

<210> SEQ ID NO 173
<211> LENGTH: 8
<212> TYPE: PRT
<213> ORGANISM: Artificial Sequence
<220> FEATURE:
<223> OTHER INFORMATION: Immunoglobulin binding ligand

<400> SEQUENCE: 173

Lys Tyr Trp Tyr Gln Lys Trp Phe
1               5

<210> SEQ ID NO 174
<211> LENGTH: 12
<212> TYPE: PRT
<213> ORGANISM: Artificial Sequence
<220> FEATURE:
<223> OTHER INFORMATION: Immunoglobulin binding ligand

<400> SEQUENCE: 174
```

```
His Tyr Thr Thr Tyr Lys Ser Tyr Ile Ser Ile Phe
1               5                   10
```

<210> SEQ ID NO 175
<211> LENGTH: 12
<212> TYPE: PRT
<213> ORGANISM: Artificial Sequence
<220> FEATURE:
<223> OTHER INFORMATION: Immunoglobulin binding ligand

<400> SEQUENCE: 175

```
Glu Met Arg Val Tyr Thr Ser His Leu Ser Tyr His
1               5                   10
```

<210> SEQ ID NO 176
<211> LENGTH: 12
<212> TYPE: PRT
<213> ORGANISM: Artificial Sequence
<220> FEATURE:
<223> OTHER INFORMATION: Immunoglobulin binding ligand

<400> SEQUENCE: 176

```
Val Ser Thr Val Ser Tyr Ser Phe Leu Gln Arg Ser
1               5                   10
```

<210> SEQ ID NO 177
<211> LENGTH: 12
<212> TYPE: PRT
<213> ORGANISM: Artificial Sequence
<220> FEATURE:
<223> OTHER INFORMATION: Immunoglobulin binding ligand

<400> SEQUENCE: 177

```
Ser Gly Ser Tyr Ala Pro Pro Met Ser Arg Tyr Ser
1               5                   10
```

<210> SEQ ID NO 178
<211> LENGTH: 12
<212> TYPE: PRT
<213> ORGANISM: Artificial Sequence
<220> FEATURE:
<223> OTHER INFORMATION: Immunoglobulin binding ligand

<400> SEQUENCE: 178

```
Trp Thr Lys Thr Ser Ser Ile Ser Phe Lys Thr Pro
1               5                   10
```

<210> SEQ ID NO 179
<211> LENGTH: 12
<212> TYPE: PRT
<213> ORGANISM: Artificial Sequence
<220> FEATURE:
<223> OTHER INFORMATION: Immunoglobulin binding ligand

<400> SEQUENCE: 179

```
Ser Trp Tyr Lys Ser Ser Ile Ser Ser Lys Gln Phe
1               5                   10
```

<210> SEQ ID NO 180

<400> SEQUENCE: 180

000

<210> SEQ ID NO 181
<211> LENGTH: 6
<212> TYPE: PRT

```
<213> ORGANISM: Artificial Sequence
<220> FEATURE:
<223> OTHER INFORMATION: Linker

<400> SEQUENCE: 181

Gly Gly Gly Ser Arg Lys
1               5

<210> SEQ ID NO 182
<211> LENGTH: 5
<212> TYPE: PRT
<213> ORGANISM: Artificial Sequence
<220> FEATURE:
<223> OTHER INFORMATION: Linker

<400> SEQUENCE: 182

Gly Gly Gly Ser Lys
1               5

<210> SEQ ID NO 183
<211> LENGTH: 6
<212> TYPE: PRT
<213> ORGANISM: Artificial Sequence
<220> FEATURE:
<223> OTHER INFORMATION: Linker

<400> SEQUENCE: 183

Gly Gly Gly Ser Lys Lys
1               5

<210> SEQ ID NO 184
<211> LENGTH: 11
<212> TYPE: PRT
<213> ORGANISM: Artificial Sequence
<220> FEATURE:
<223> OTHER INFORMATION: control biotin-labelled synthetic peptide
<220> FEATURE:
<221> NAME/KEY: MISC_FEATURE
<222> LOCATION: (11)..(11)
<223> OTHER INFORMATION: epsilon-biotin

<400> SEQUENCE: 184

Gly Asn Trp Thr Leu Gly Gly Tyr Lys Gly Lys
1               5                   10

<210> SEQ ID NO 185
<211> LENGTH: 11
<212> TYPE: PRT
<213> ORGANISM: Artificial Sequence
<220> FEATURE:
<223> OTHER INFORMATION: control biotin-labelled synthetic peptide
<220> FEATURE:
<221> NAME/KEY: MISC_FEATURE
<222> LOCATION: (11)..(11)
<223> OTHER INFORMATION: epsilon-biotin

<400> SEQUENCE: 185

His Lys Val Thr Ser Tyr Leu Gly Gly Gly Lys
1               5                   10

<210> SEQ ID NO 186
<211> LENGTH: 10
<212> TYPE: PRT
<213> ORGANISM: Artificial Sequence
<220> FEATURE:
<223> OTHER INFORMATION: Variant

<400> SEQUENCE: 186
```

```
Gly Asn Gly Ser Tyr Trp Tyr Gln Val Trp
1               5                   10

<210> SEQ ID NO 187
<211> LENGTH: 6
<212> TYPE: PRT
<213> ORGANISM: Artificial Sequence
<220> FEATURE:
<223> OTHER INFORMATION: Variant

<400> SEQUENCE: 187

Gly Asn Gly Ser Tyr Trp
1               5

<210> SEQ ID NO 188
<211> LENGTH: 4
<212> TYPE: PRT
<213> ORGANISM: Artificial Sequence
<220> FEATURE:
<223> OTHER INFORMATION: Variant

<400> SEQUENCE: 188

Gly Ser Tyr Trp
1

<210> SEQ ID NO 189
<211> LENGTH: 8
<212> TYPE: PRT
<213> ORGANISM: Artificial Sequence
<220> FEATURE:
<223> OTHER INFORMATION: Variant

<400> SEQUENCE: 189

Gly Ser Tyr Trp Tyr Gln Val Trp
1               5

<210> SEQ ID NO 190
<211> LENGTH: 7
<212> TYPE: PRT
<213> ORGANISM: Artificial Sequence
<220> FEATURE:
<223> OTHER INFORMATION: Variant

<400> SEQUENCE: 190

Gly Trp Tyr Gln Val Trp Phe
1               5

<210> SEQ ID NO 191
<211> LENGTH: 5
<212> TYPE: PRT
<213> ORGANISM: Artificial Sequence
<220> FEATURE:
<223> OTHER INFORMATION: Variant

<400> SEQUENCE: 191

Gly Tyr Gln Val Trp
1               5

<210> SEQ ID NO 192
<211> LENGTH: 9
<212> TYPE: PRT
<213> ORGANISM: Artificial Sequence
<220> FEATURE:
<223> OTHER INFORMATION: Variant

<400> SEQUENCE: 192

Gly Ser Tyr Ala Tyr Gln Val Trp Phe
```

```
1               5

<210> SEQ ID NO 193
<211> LENGTH: 9
<212> TYPE: PRT
<213> ORGANISM: Artificial Sequence
<220> FEATURE:
<223> OTHER INFORMATION: Variant

<400> SEQUENCE: 193

Gly Ser Tyr Trp Ala Gln Val Trp Phe
1               5

<210> SEQ ID NO 194
<211> LENGTH: 9
<212> TYPE: PRT
<213> ORGANISM: Artificial Sequence
<220> FEATURE:
<223> OTHER INFORMATION: Variant

<400> SEQUENCE: 194

Gly Ser Tyr Trp Tyr Gln Val Ala Phe
1               5

<210> SEQ ID NO 195
<211> LENGTH: 9
<212> TYPE: PRT
<213> ORGANISM: Artificial Sequence
<220> FEATURE:
<223> OTHER INFORMATION: Variant

<400> SEQUENCE: 195

Gly Ser Tyr Trp Tyr Gln Asp Trp Phe
1               5

<210> SEQ ID NO 196
<211> LENGTH: 9
<212> TYPE: PRT
<213> ORGANISM: Artificial Sequence
<220> FEATURE:
<223> OTHER INFORMATION: Variant

<400> SEQUENCE: 196

Gly Ser Tyr Trp Tyr Gln Ser Trp Phe
1               5

<210> SEQ ID NO 197
<211> LENGTH: 9
<212> TYPE: PRT
<213> ORGANISM: Artificial Sequence
<220> FEATURE:
<223> OTHER INFORMATION: Variant

<400> SEQUENCE: 197

Gly Ser Tyr Trp Tyr Gln Asn Trp Phe
1               5

<210> SEQ ID NO 198
<211> LENGTH: 9
<212> TYPE: PRT
<213> ORGANISM: Artificial Sequence
<220> FEATURE:
<223> OTHER INFORMATION: Variant

<400> SEQUENCE: 198

Gly Ser Tyr Trp Tyr Asp Ser Trp Phe
1               5
```

```
<210> SEQ ID NO 199
<211> LENGTH: 9
<212> TYPE: PRT
<213> ORGANISM: Artificial Sequence
<220> FEATURE:
<223> OTHER INFORMATION: Variant

<400> SEQUENCE: 199

Gly Ser Tyr Trp Tyr Asp Asn Trp Phe
1               5

<210> SEQ ID NO 200
<211> LENGTH: 9
<212> TYPE: PRT
<213> ORGANISM: Artificial Sequence
<220> FEATURE:
<223> OTHER INFORMATION: Variant

<400> SEQUENCE: 200

Gly Asp Tyr Trp Tyr Asp Val Trp Phe
1               5

<210> SEQ ID NO 201
<211> LENGTH: 15
<212> TYPE: PRT
<213> ORGANISM: Artificial Sequence
<220> FEATURE:
<223> OTHER INFORMATION: immunoglobulin binding ligand with C-terminal
      linker
<220> FEATURE:
<221> NAME/KEY: MISC_FEATURE
<222> LOCATION: (15)..(15)
<223> OTHER INFORMATION: epsilon-biotin

<400> SEQUENCE: 201

Gly Ser Tyr Trp Tyr Gln Val Trp Phe Gly Gly Gly Ser Arg Lys
1               5                   10                  15

<210> SEQ ID NO 202
<211> LENGTH: 9
<212> TYPE: PRT
<213> ORGANISM: Artificial Sequence
<220> FEATURE:
<223> OTHER INFORMATION: Immunoglobulin binding ligand
<220> FEATURE:
<221> NAME/KEY: misc_feature
<222> LOCATION: (1)..(9)
<223> OTHER INFORMATION: Xaa can be any naturally occurring amino acid

<400> SEQUENCE: 202

Xaa Xaa Xaa Xaa Xaa Xaa Xaa Xaa Xaa
1               5

<210> SEQ ID NO 203
<211> LENGTH: 9
<212> TYPE: PRT
<213> ORGANISM: Artificial Sequence
<220> FEATURE:
<223> OTHER INFORMATION: Immunoglobulin binding ligand
<220> FEATURE:
<221> NAME/KEY: misc_feature
<222> LOCATION: (1)..(7)
<223> OTHER INFORMATION: Xaa can be any naturally occurring amino acid

<400> SEQUENCE: 203

Xaa Xaa Xaa Xaa Xaa Xaa Xaa Trp Phe
1               5
```

<210> SEQ ID NO 204
<211> LENGTH: 9
<212> TYPE: PRT
<213> ORGANISM: Artificial Sequence
<220> FEATURE:
<223> OTHER INFORMATION: Immunoglobulin binding ligand
<220> FEATURE:
<221> NAME/KEY: misc_feature
<222> LOCATION: (1)..(9)
<223> OTHER INFORMATION: Xaa can be any naturally occurring amino acid

<400> SEQUENCE: 204

Xaa Xaa Xaa Xaa Xaa Xaa Xaa Xaa Xaa
1               5

<210> SEQ ID NO 205
<211> LENGTH: 5
<212> TYPE: PRT
<213> ORGANISM: Artificial Sequence
<220> FEATURE:
<223> OTHER INFORMATION: Linker

<400> SEQUENCE: 205

Gly Gly Asp Asp Lys
1               5

<210> SEQ ID NO 206
<211> LENGTH: 5
<212> TYPE: PRT
<213> ORGANISM: Artificial Sequence
<220> FEATURE:
<223> OTHER INFORMATION: Linker

<400> SEQUENCE: 206

Gly Gly Asp Ser Lys
1               5

<210> SEQ ID NO 207
<211> LENGTH: 4
<212> TYPE: PRT
<213> ORGANISM: Artificial Sequence
<220> FEATURE:
<223> OTHER INFORMATION: Synthetic

<400> SEQUENCE: 207

Gly Gly Gly Gly
1

<210> SEQ ID NO 208
<211> LENGTH: 4
<212> TYPE: PRT
<213> ORGANISM: Artificial Sequence
<220> FEATURE:
<223> OTHER INFORMATION: Synthetic

<400> SEQUENCE: 208

Gly Ser Gly Gly
1

<210> SEQ ID NO 209
<211> LENGTH: 4
<212> TYPE: PRT
<213> ORGANISM: Artificial Sequence
<220> FEATURE:
<223> OTHER INFORMATION: Synthetic

<400> SEQUENCE: 209

Gly Gly Ser Gly
1

<210> SEQ ID NO 210
<211> LENGTH: 4
<212> TYPE: PRT
<213> ORGANISM: Artificial Sequence
<220> FEATURE:
<223> OTHER INFORMATION: Synthetic

<400> SEQUENCE: 210

Gly Gly Gly Ser
1

<210> SEQ ID NO 211
<211> LENGTH: 5
<212> TYPE: PRT
<213> ORGANISM: Artificial Sequence
<220> FEATURE:
<223> OTHER INFORMATION: Synthetic

<400> SEQUENCE: 211

Gly Ser Gly Gly Ser
1               5

<210> SEQ ID NO 212
<211> LENGTH: 5
<212> TYPE: PRT
<213> ORGANISM: Artificial Sequence
<220> FEATURE:
<223> OTHER INFORMATION: Synthetic

<400> SEQUENCE: 212

Gly Gly Gly Gly Ser
1               5

<210> SEQ ID NO 213
<211> LENGTH: 6
<212> TYPE: PRT
<213> ORGANISM: Artificial Sequence
<220> FEATURE:
<223> OTHER INFORMATION: Synthetic

<400> SEQUENCE: 213

Gly Gly Ser Gly Gly Ser
1               5

<210> SEQ ID NO 214
<211> LENGTH: 8
<212> TYPE: PRT
<213> ORGANISM: Artificial Sequence
<220> FEATURE:
<223> OTHER INFORMATION: Synthetic

<400> SEQUENCE: 214

Gly Gly Ser Gly Gly Ser Gly
1               5

<210> SEQ ID NO 215
<211> LENGTH: 8
<212> TYPE: PRT
<213> ORGANISM: Artificial Sequence
<220> FEATURE:
<223> OTHER INFORMATION: Synthetic

<400> SEQUENCE: 215

Gly Gly Gly Ser Gly Gly Gly Ser

-continued

```
<210> SEQ ID NO 216
<211> LENGTH: 10
<212> TYPE: PRT
<213> ORGANISM: Artificial Sequence
<220> FEATURE:
<223> OTHER INFORMATION: Synthetic

<400> SEQUENCE: 216

Gly Ser Gly Gly Ser Gly Ser Gly Gly Ser
1               5                   10

<210> SEQ ID NO 217
<211> LENGTH: 10
<212> TYPE: PRT
<213> ORGANISM: Artificial Sequence
<220> FEATURE:
<223> OTHER INFORMATION: Synthetic

<400> SEQUENCE: 217

Gly Gly Gly Gly Ser Gly Gly Gly Gly Ser
1               5                   10

<210> SEQ ID NO 218
<211> LENGTH: 19
<212> TYPE: PRT
<213> ORGANISM: Artificial Sequence
<220> FEATURE:
<223> OTHER INFORMATION: Synthetic

<400> SEQUENCE: 218

His Asp Phe Leu Phe Leu Tyr Asp Trp Leu Lys Leu Val Leu Phe Asp
1               5                   10                  15

Phe Asn His
```

AFFINITY LIGANDS FOR ANTIBODY Fc REGION

CROSS-REFERENCE TO RELATED APPLICATIONS

This application is a national phase application under 35 U.S.C. § 371 of PCT International Application No. PCT/EP2019/052484, filed Feb. 1, 2019, which claims the benefit of Luxembourg Patent Application No. LU100693, filed Feb. 2, 2018, each of which is herein incorporated by reference.

SEQUENCE LISTING

The instant application contains a Sequence Listing which has been submitted electronically in ASCII format and is hereby incorporated by reference in its entirety. Said ASCII copy, created on May 12, 2023, is named 38571-251_SQL_ST25_Corr_May 12, 2023 and is 43,430 bytes in size.

A. FIELD OF THE INVENTION

The present invention relates to affinity ligands having binding affinity for immunoglobulins, and methods of using such compounds. Such methods enable detection and purification of immunoglobulins and recombinant proteins containing immunoglobulin Fc fragments from liquids such as, but not limited to, blood plasma, plasma fractions, ascites fluid, cell culture media and milk. Said methods further enable formation of multimeric antibody complexes and attachment of antibodies to therapeutic carriers and solid matrices.

B. BACKGROUND OF THE INVENTION

In recent decades, monoclonal antibodies (mAbs) and Fc fusion proteins have emerged as dominant biopharmaceuticals for the diagnosis and treatment of various diseases. Representatives of both groups range from orphan drugs to those being administered to a large population of patients (1). The main reason for widespread use of mAbs as diagnostic and therapeutic agents is their high specificity. Therapeutic antibodies recognize and neutralize pathogenic or mutated proteins and cells with high specificity, while having acceptable patient tolerability following administration. All currently approved therapeutic monoclonal antibodies and the majority of those in clinical trials are manufactured using mammalian cell cultures (2, 3).

Recombinant antibody purification is often a multistep process, with affinity chromatography representing the central procedure owing to high selectivity, rapid turnaround time and simplicity. Affinity chromatography is commonly based on bacterial immunoglobulin (Ig)-binding proteins such as staphylococcal protein A (SpA) and streptococcal protein G (SpG) (4, 5). Due to high specificity of bacterial Ig-binding proteins, it is widely employed as a capture step of choice by majority of industrial antibody manufacturers (6). However, the use of natural immunoglobulin-binding proteins as affinity ligands suffers from several drawbacks (4). One of them is that protein A does not bind all human IgG subclasses, such as $IgG_3$. Furthermore, both bacterial immunoglobulin Ig-binding proteins are isolated from bacteria, leading to high cost and possible contamination of the final product. Affinity chromatography based on protein A or protein G columns requires relatively harsh elution conditions that can negatively impact the structure and function of recombinant antibodies, which raises concerns over the products' immunogenicity profile. Moreover, instability of affinity ligands (especially under elution and column sanitization conditions) dictates high costs due to relatively short column shelf life and efforts required to eliminate the leached ligands from the final product (7, 8).

Hence, there is increasing interest in development of alternative antibody ligands to improve affinity chromatography methods (9). Considering all the drawbacks, so far affinity matrix manufacturers have focused on providing alternative affinity ligands which are mainly engineered variants of bacterial Ig-binding proteins or their fragments (e.g., TRPA (Thermal Responsive Protein A) (10) or Z domain (11)) with improved characteristics. However, despite implementation of such alternative matrices into purification process, an additional chromatography polishing step is needed in order to achieve appropriate purity of the final product (12). New advanced computational tools for molecular design provide (bio)chemists with better understanding of the molecular recognition phenomena and therefore, enable the design of more effective affinity ligands. Several small synthetic immunoglobulin ligands were designed based on structural data of antibody-natural Ig-binding protein complexes (13). Finally, some peptide affinity ligands with unique structures were identified from chemical libraries and engineered using different molecular display methodologies (12).

Short linear peptides are affordable and can be rapidly synthesized even on a relatively large scale (14, 15). Their stability is relatively high compared to larger proteins that rely on complex folding pattern required for formation of binding sites. Furthermore, for short peptide ligands binding affinity to target proteins can be adjusted to achieve moderate affinity, which allows mild conditions for breaking the interaction with the Ig molecule, thus exposing the antibody to minor stress.

C. SUMMARY OF THE INVENTION

The invention refers to ligands having specific binding affinity for immunoglobulins, and the use of said affinity ligands. The affinity ligands of the invention are used for purification or detection of immunoglobulins and recombinant Fc-fusion proteins, as well as formation of ligand-antibody complexes for tethering drugs, diagnostic agents, and reporter groups to the antibody via coupling or fusion to the ligand moiety. In another embodiment of the invention, the affinity ligands, preferably covalently coupled to a solid support, are employed as capturing agents for immobilization of antibodies or Fc-fusion proteins onto solid supports such as, but not limited to, biosensor surfaces and immunoprecipitation matrices. Moreover, the affinity ligands are employed as capturing agents on surfaces of drug or gene delivery systems (e.g., nanoparticles or liposomes). The present invention also refers to branched multimers of said short affinity ligand (e.g., tetramers or dendrimers) and their use for cross-linking multiple antibody molecules. The said ligands are preferably peptides or mimetics thereof.

Specifically, the present invention encompasses the following items [1] to [106].

[1] An immunoglobulin binding ligand having the following structure:

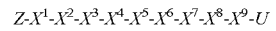

wherein $X^1$ may or may not be present, but if present it can be any amino acid, preferably G; $X^2$ may or may not be present, but if present it is a hydrophilic (polar) amino acid, preferably S, T, C, N or K; $X^3$ is a hydrophobic, aromatic amino acid, preferentially Y; $X^4$ is a hydrophobic, aromatic amino acid, preferentially W; $X^5$ is a hydrophobic, aromatic amino acid, preferentially Y; $X^6$ can be any amino acid but preferably is one bearing a negative charge (for example D and E), or A or Q or K; $X^7$ can be any amino acid but preferably is a small hydrophobic amino acid (for example V or A) or K; $X^8$ is a hydrophobic, aromatic amino acid, preferentially W; $X^9$ is a hydrophobic, aromatic amino acid, preferentially F; Z is a hydrogen atom replacing the N-terminal amino group or an N-terminal amino group, or it is a linker or a capping group, bound either to the N-terminal amino group or directly to the alpha C-atom of the N-terminal residue; and U is a hydrogen atom replacing the C-terminal carboxyl group or a C-terminal carboxyl group, or is a linker or a capping group, bound either to the C-terminal carbonyl group or directly to the alpha C-atom of the C-terminal residue; optionally with the following proviso applying: if $X^1$ is present and $X^2$ is not present, then $X^1$ is not D-Phe.

[2] The ligand of item [1], wherein $X^1$ is not present.
[3] The ligand of item [1], wherein $X^1$ is present.
[4] The ligand of item [3], wherein $X^1$ is G or A.
[5] The ligand of item [3], wherein $X^1$ is G.
[6] The ligand of any one of items [1] to [5], wherein $X^2$ is not present.
[7] The ligand of any one of items [1] to [5], wherein $X^2$ is present.
[8] The ligand of item [7], wherein $X^2$ is S, T, C, N or K.
[9] The ligand of item [7], wherein $X^2$ is S.
[10] The ligand of item [7], wherein $X^2$ is T.
[11] The ligand of item [7], wherein $X^2$ is C.
[12] The ligand of item [7], wherein $X^2$ is N.
[13] The ligand of item [7], wherein $X^2$ is K.
[14] The ligand of any one of items [1] to [13], wherein $X^3$ is Y, W or F.
[15] The ligand of any one of items [1] to [13], wherein $X^3$ is Y.
[16] The ligand of any one of items [1] to [13], wherein $X^3$ is W.
[17] The ligand of any one of items [1] to [13], wherein $X^3$ is F.
[18] The ligand of any one of items [1] to [17], wherein $X^4$ is W, Y or F.
[19] The ligand of any one of items [1] to [17], wherein $X^4$ is W.
[20] The ligand of any one of items [1] to [17], wherein $X^4$ is Y.
[21] The ligand of any one of items [1] to [17], wherein $X^4$ is F.
[22] The ligand of any one of items [1] to [21], wherein $X^5$ is Y, W or F.
[23] The ligand of any one of items [1] to [21], wherein $X^5$ is Y.
[24] The ligand of any one of items [1] to [21], wherein $X^5$ is W.
[25] The ligand of any one of items [1] to [21], wherein $X^5$ is F.
[26] The ligand of any one of items [1] to [25], wherein $X^6$ is an amino acid bearing a negative charge.
[27] The ligand of any one of items [1] to [25], wherein $X^6$ is A, D, E, N, Q or K.
[28] The ligand of any one of items [1] to [25], wherein $X^6$ is A.
[29] The ligand of any one of items [1] to [25], wherein $X^6$ is D.
[30] The ligand of any one of items [1] to [25], wherein $X^6$ is E.
[31] The ligand of any one of items [1] to [25], wherein $X^6$ is N.
[32] The ligand of any one of items [1] to [25], wherein $X^6$ is Q.
[33] The ligand of any one of items [1] to [25], wherein $X^6$ is K.
[34] The ligand of any one of items [1] to [33], wherein $X^7$ is a small hydrophobic amino acid.
[35] The ligand of any one of items [1] to [33], wherein $X^7$ is V, A, K, C, I, L or M.
[36] The ligand of any one of items [1] to [33], wherein $X^7$ is V.
[37] The ligand of any one of items [1] to [33], wherein $X^7$ is A.
[38] The ligand of any one of items [1] to [33], wherein $X^7$ is K.
[39] The ligand of any one of items [1] to [33], wherein $X^7$ is C.
[40] The ligand of any one of items [1] to [33], wherein $X^7$ is I.
[41] The ligand of any one of items [1] to [33], wherein $X^7$ is L.
[42] The ligand of any one of items [1] to [33], wherein $X^7$ is M.
[43] The ligand of any one of items [1] to [42], wherein $X^8$ is W, Y or F.
[44] The ligand of any one of items [1] to [42], wherein $X^8$ is W.
[45] The ligand of any one of items [1] to [42], wherein $X^8$ is Y.
[46] The ligand of any one of items [1] to [42], wherein $X^8$ is F.
[47] The ligand of any one of items [1] to [46], wherein $X^9$ is F, W or Y.
[48] The ligand of any one of items [1] to [46], wherein $X^9$ is F.
[49] The ligand of any one of items [1] to [46], wherein $X^9$ is W.
[50] The ligand of any one of items [1] to [46], wherein $X^9$ is Y.
[51] The ligand of any one of items [1] to [50], wherein Z is a hydrogen atom replacing the N-terminal amino group.
[52] The ligand of any one of items [1] to [50], wherein Z is an N-terminal amino group.
[53] The ligand of any one of items [1] to [50], wherein Z is a linker or a capping group, bound either to the N-terminal amino group or directly to the alpha C-atom of the N-terminal residue.
[54] The ligand of any one of items [1] to [50], wherein Z is a linker, bound either to the N-terminal amino group or directly to the alpha C-atom of the N-terminal residue.
[55] The ligand of any one of items [1] to [50], wherein Z is a capping group, bound either to the N-terminal amino group or directly to the alpha C-atom of the N-terminal residue.
[56] The ligand of any one of items [1] to [55], wherein U is a hydrogen atom replacing the C-terminal carboxyl group.
[57] The ligand of any one of items [1] to [55], wherein U is a C-terminal carboxyl group.

[58] The ligand of any one of items [1] to [55], wherein U is a linker or a capping group, bound either to the C-terminal carbonyl group or directly to the alpha C-atom of the C-terminal residue.
[59] The ligand of any one of items [1] to [55], wherein U is a linker, bound either to the C-terminal carbonyl group or directly to the alpha C-atom of the C-terminal residue.
[60] The ligand of any one of items [1] to [55], wherein U is a capping group, bound either to the C-terminal carbonyl group or directly to the alpha C-atom of the C-terminal residue.
[61] The ligand of any one of items [1] to [60], wherein one or more amino acids of said ligand are in L-form or D-form, or wherein the amino acids of said ligand are a combination of both L- and D-forms.
[62] The ligand of any one of items [1] to [60], wherein one or more amino acids of said ligand are in L-form.
[63] The ligand of any one of items [1] to [60], wherein one or more amino acids of said ligand are in D-form.
[64] The ligand of any one of items [1] to [60], wherein the amino acids of said ligand are a combination of both L- and D-forms.
[65] The ligand of any one of items [1] to [64], wherein the ligand comprises an amino acid sequence having at least 60%, such as at least 70%, sequence identity with any one of the amino acid sequences SEQ ID NO: 1 to SEQ ID NO: 173.
[66] The ligand of item [65], wherein one or more (such as two or more) amino acids in the reference sequence SEQ ID NO: 1 to SEQ ID NO: 173 are substituted by conservative substitutions.
[67] The ligand of any one of items [1] to [65], wherein the ligand comprises any one of the amino acid sequences SEQ ID NO: 1 to SEQ ID NO: 173.
[68] The ligand of any one of items [1] to [65], wherein the ligand consists of any one of the amino acid sequences SEQ ID NO: 1 to SEQ ID NO: 173.
[69] The ligand comprising an amino acid sequence having at least 60%, such as at least 70%, sequence identity with any one of the amino acid sequences SEQ ID NO: 174 to SEQ ID NO: 179.
[70] The ligand of item [69], wherein one or more (such as two or more) amino acids in the reference sequence SEQ ID NO: 174 to SEQ ID NO: 179 are substituted by conservative substitutions.
[71] The ligand of item [69], wherein the ligand comprises any one of the amino acid sequences SEQ ID NO: 174 to SEQ ID NO: 179.
[72] The ligand of item [69], wherein the ligand consists of any one of the amino acid sequences SEQ ID NO: 174 to SEQ ID NO: 179.
[73] The ligand of any one of items [1] to [72], wherein said ligand binds to the Fc fragment of immunoglobulins.
[74] The ligand of any one of items [1] to [73], which further comprises a linking group coupled to either the C-terminal carbonyl group or directly to the alpha C-atom of C-terminal residue.
[75] The ligand of any one of items [1] to [74], which further comprises a linking group coupled to either the N-terminal amino group or directly to the alpha C-atom of N-terminal residue.
[76] A retro-inverso analogue of the ligand of any one of items [1] to [75].
[77] A peptidomimetic of the ligand of any one of items [1] to [75].

[78] The peptidomimetic of item [77], wherein one or more amino acids of the ligand are replaced by a non-standard (non-proteinogenic) amino acid other than D-amino acids.
[79] The peptidomimetic of item [77] or [78], comprising a methyl group on one or more nitrogen atoms of the peptide backbone.
[80] The peptidomimetic of item [77] or [78], wherein one or more amino acid side chains are re-located from an alpha C-atom to adjacent alpha nitrogen atom of the peptide backbone.
[81] The peptidomimetic of any one of items [77] to [79], comprising phosphonate, amidate, carbamate ester, trifluoroethylamine, or sulphonamide backbone linkages replacing the peptide backbone linkages but retaining the sequences of side chains of the ligand.
[82] A construct comprising the ligand of any one of items [1] to [75], the retro-inverso analogue of item [76] or the peptidomimetic of any one of items [77] to [81] to which a detectable group, a drug, a diagnostic agent or a duration enhancing moiety is attached.
[83] The construct of item [82], wherein the detectable group, the drug, the diagnostic agent or the duration enhancing moiety is covalently attached to ligand directly or indirectly through peptide or non-peptide linker, such as, but not limited to polyethylene glycol chain.
[84] The construct of item [82] or [83], wherein the detectable group is selected from the group consisting of haptens, biotin, fluorophores, quantum dots, groups containing radioactive isotopes, and enzymes.
[85] A recombinant bacteriophage displaying the ligand of any one of items [1] to [75].
[86] A fusion protein, containing a protein fused to the ligand of any one of items [1] to [75].
[87] A solid phase support, on which the ligand of any one of items [1] to [75], the retro-inverso analogue of item [76] or the peptidomimetic of any one of items [77] to [81] is immobilized.
[88] The solid phase support of item [87], wherein said solid phase is bead, gold surface, particle, membrane, semi-permeable membrane, monolith, capillary, microarray or multiple well plate.
[89] The solid support of item [87] or [88], where said solid support comprises inorganic material, organic material or combination of both.
[90] The solid support of any one of items [87] to [89], where said solid support comprises an organic material selected from the group including but not limited to polysaccharides such as agarose, dextran, cellulose, or chitosan; or polyacrylamide, or polyacrylate, or polystyrene, or polyvinyl alcohol, or combination of thereof.
[91] A polynucleotide, such as DNA, comprising a nucleic acid sequence encoding the ligand of any one of items [1] to [75].
[92] A vector comprising the polynucleotide of item [91].
[93] A transformant comprising the vector of item [92].
[94] A kit for detecting or purifying immunoglobulins or Fc region-containing proteins, comprising at least one of the following components: the ligand of any one of items [1] to [75], the retro-inverso analogue of item [76], the peptidomimetic of any one of items [77] to [81], the construct of any one of items [82] to [84]; the recombinant bacteriophage of item [85], the fusion protein of item [86], the solid phase support of any one of items [87] to [90], the polynucleotide of item [91], the vector of item [92] and the transformant of item [93].

[95] A method for detecting immunoglobulins or Fc region-containing proteins thereof in a sample, comprising the steps a) to c):
  a) providing a ligand of any one of items [1] to [75], a retro-inverso analogue of item [76] or a peptidomimetic of any one of items [77] to [81];
  b) contacting said ligand, retro-inverso analogue or peptidomimetic with a composition containing an immunoglobulin or Fc region-containing protein; and
  c) measuring the level of binding produced in step b) between the ligand, retro-inverso analogue or peptidomimetic and immunoglobulins or Fc region-containing proteins thereof.

[96] The method of item [94], wherein the level of binding is measured by surface plasmon resonance biosensor, piezoelectric biosensor, ELISA, FLISA, electrochemiluminescence-based assay, or bio-layer interferometry.

[97] A method for purifying immunoglobulins or Fc region-containing proteins thereof in a sample, comprising the steps a) to c):
  a) contacting a ligand of any one of items [1] to [75], a retro-inverso analogue of item [76] or a peptidomimetic of any one of items [77] to [81] with a sample containing immunoglobulins or Fc region-containing proteins, thereby binding immunoglobulins or Fc region-containing proteins thereof in the sample to the ligand, retro-inverso analogue or peptidomimetic;
  b) separating the immunoglobulins or the Fc region-containing proteins thereof, which are bound to the ligand, retro-inverso analogue or peptidomimetic in step a), from the sample; and
  c) detaching and eluting the immunoglobulins or the Fc region-containing proteins thereof, from the ligand, retro-inverso analogue or peptidomimetic.

[98] A method for eliminating immunoglobulins or Fc region-containing proteins thereof from a sample, comprising the steps a) and b):
  a) contacting a ligand of any one of items [1] to [75], a retro-inverso analogue of item [76] or a peptidomimetic of any one of items [77] to [81] with a sample containing immunoglobulins or Fc region-containing proteins, thereby binding immunoglobulins or Fc region-containing proteins thereof in the sample to the ligand, retro-inverso analogue or peptidomimetic; and
  b) removing immunoglobulins or Fc region-containing proteins thereof, which are bound to the ligand, retro-inverso analogue or peptidomimetic in step a), from the sample.

[99] A method for purifying a fusion protein from a sample, comprising the steps a) to c):
  a) providing sample containing a fusion protein containing a protein of interest linked to a ligand of any one of items [1] to [75];
  b) contacting the sample provided in step a) with immobilized immunoglobulins, Fc fragments or Fc region-containing proteins thereof, thereby binding the fusion protein to the immunoglobulins, Fc fragments or Fc region-containing proteins thereof; and
  c) separating the fusion protein, which is bound to the immobilized immunoglobulins or Fc region-containing proteins thereof in step b), from the sample.

[100] A method for non-covalent labelling of immunoglobulins or fusion proteins containing Fc region of immunoglobulin, comprising the steps a) to b):
  a) preparing a construct consisting of a ligand of any one of items [1] to [75], a retro-inverso analogue of item [76] or a peptidomimetic of any one of items [77] to [81] conjugated to a detectable group, a drug, a diagnostic agent or a duration enhancing moiety (such as, but not limited to, polyethylene glycol); and
  b) contacting an antibody or fusion protein containing Fc region of immunoglobulin with the construct prepared in step a) to form a complex consisting of the construct and the antibody or fusion protein containing Fc region of immunoglobulin.

[101] A method for immobilizing immunoglobulins or fusion proteins containing Fc region of immunoglobulin onto solid supports, comprising the steps a) to b):
  a) coupling the a ligand of any one of items [1] to [75], a retro-inverso analogue of item [76] or a peptidomimetic of any one of items [77] to [81] onto a solid support (such as, but not limited to, biosensor surface or immunoprecipitation matrix);
  b) contacting immunoglobulins or fusion proteins containing Fc region of immunoglobulin with the solid supports of a).

[102] A method for non-covalent labelling of immunoglobulins or Fc region-containing recombinant fusion protein, comprising the steps a) to b):
  a) providing a ligand of any one of items [1] to [75], a retro-inverso analogue of item [76] or a peptidomimetic of any one of items [77] to [81]; and
  b) contacting a sample containing an immunoglobulin or an Fc region-containing recombinant fusion protein with said ligand, retro-inverso analogue or peptidomimetic of step a) to form a complex consisting of the ligand, retro-inverso analogue or peptidomimetic and the immunoglobulin or Fc region-containing recombinant fusion protein.

[103] A method for non-covalent multimerization of immunoglobulins or Fc region-containing fusion proteins comprising the steps a) to b):
  a) providing a dimer, oligomer or dendrimer of a ligand of any one of items [1] to [75], a retro-inverso analogue of item [76] or a peptidomimetic of any one of items [77] to [81]; and
  b) contacting a sample containing an immunoglobulin or an Fc region-containing fusion protein with said dimer, oligomer or dendrimer of the ligand, retro-inverso analogue or peptidomimetic of step a) to form a multimeric complex consisting of said dimer, oligomer or dendrimer of the ligand, retro-inverso analogue or peptidomimetic and one or more molecules of said immunoglobulin or Fc region-containing fusion protein.

[104] The method of any one of items [95] to [98], [102] and [103], wherein said sample comprises blood or blood plasma, plasma fractions, ascites fluid, milk, colostrum, aqueous solution containing immunoglobulins or Fc region-containing recombinant fusion proteins, or aqueous cell culture or growth medium containing immunoglobulins or Fc region-containing recombinant fusion proteins.

[105] The method of any one of items [95] to [104], wherein the ligand of any of items [1] to [75], the retro-inverso analogue of [76] or the peptidomimetic of any of items [77] to [81] is coupled to a solid support according to any one of items [88] to [90].

[106] The method of any one of items [95] to [105], wherein said contacting step is carried out in solution.

The present invention is explained in greater details in the following Sections.

D. BRIEF DESCRIPTION OF THE DRAWINGS

FIG. 1: Relative binding of selected phage clones displaying peptides with amino acid sequences identical to SEQ ID NO: 1 and SEQ ID NOs: 174-179 to human IgG Fc as determined by ELISA assay. Phage clones were identified from a phage display library via affinity selection.

Figure 2:
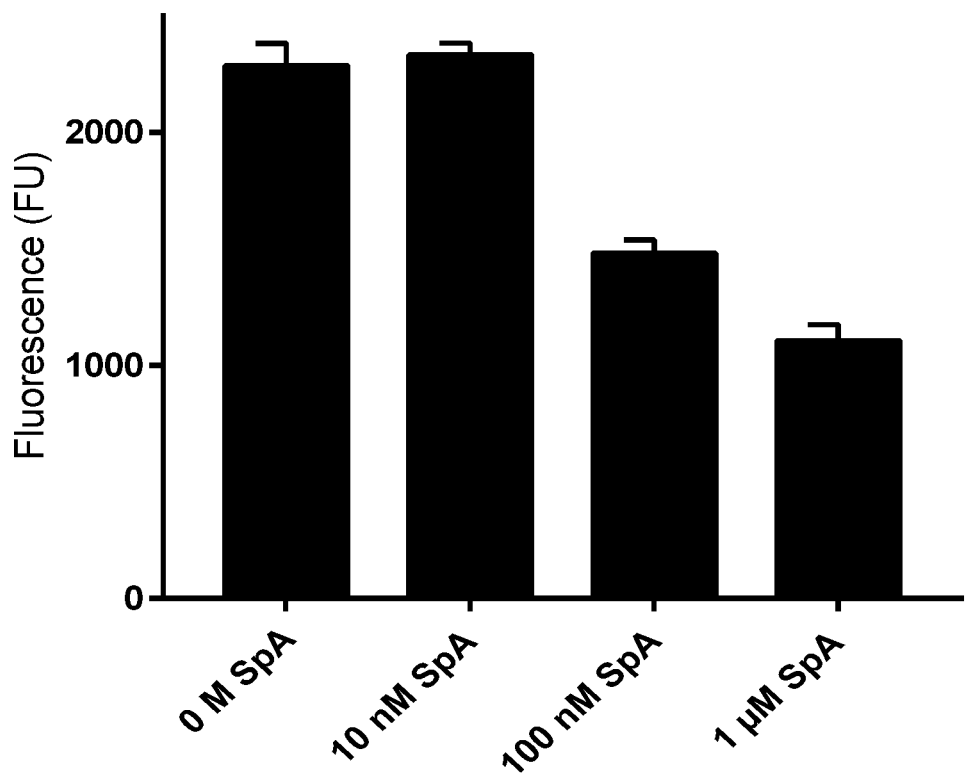

FIG. 2: The inhibition of binding of FITC-labelled phage clone displaying the peptide with amino acid sequence identical to SEQ ID NO: 1 to the immobilized human IgG Fc fragment with Staphylococcal protein A. The FITC-labelled Fc-specific phage clone ($1.2 \times 10^{10}$ pfu) was incubated in IgG Fc-coated wells together with increasing protein A (SpA) concentrations and the bound phages were detected by measuring fluorescence intensity after stringent washing.

Figure 3:
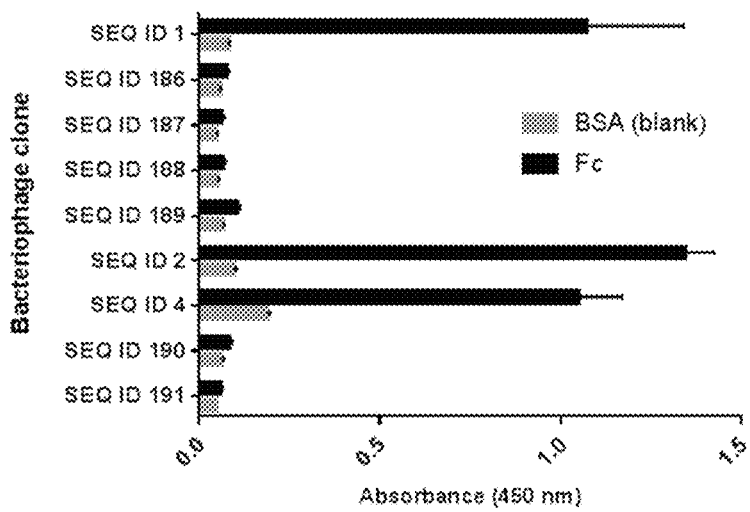

FIG. 3: Relative binding of different truncated variants of the peptide with amino acid sequence identical to SEQ ID NO: 1, SEQ ID NO: 2 and SEQ ID NOs: 186-191 to human IgG Fc fragment. Truncated variants were displayed as fusion to P3 phage coat protein on phage particles. Binding was assessed by phage ELISA assay.

Figure 4:
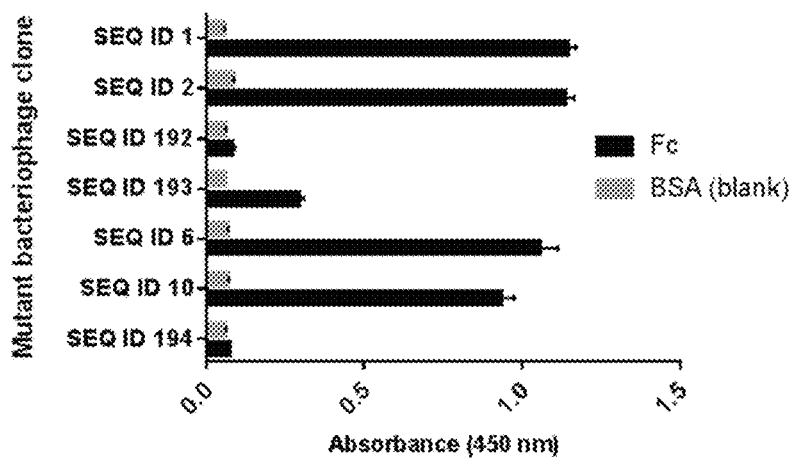

FIG. 4: Relative binding of different variants of the peptide with amino acid sequence identical to SEQ ID NO: 2 with alanine substitutions at each of the positions 4 to 8, to human IgG Fc fragment as assessed by phage ELISA assay. Individual variants were displayed on phage particles as P3 fusion.

Figure 5:
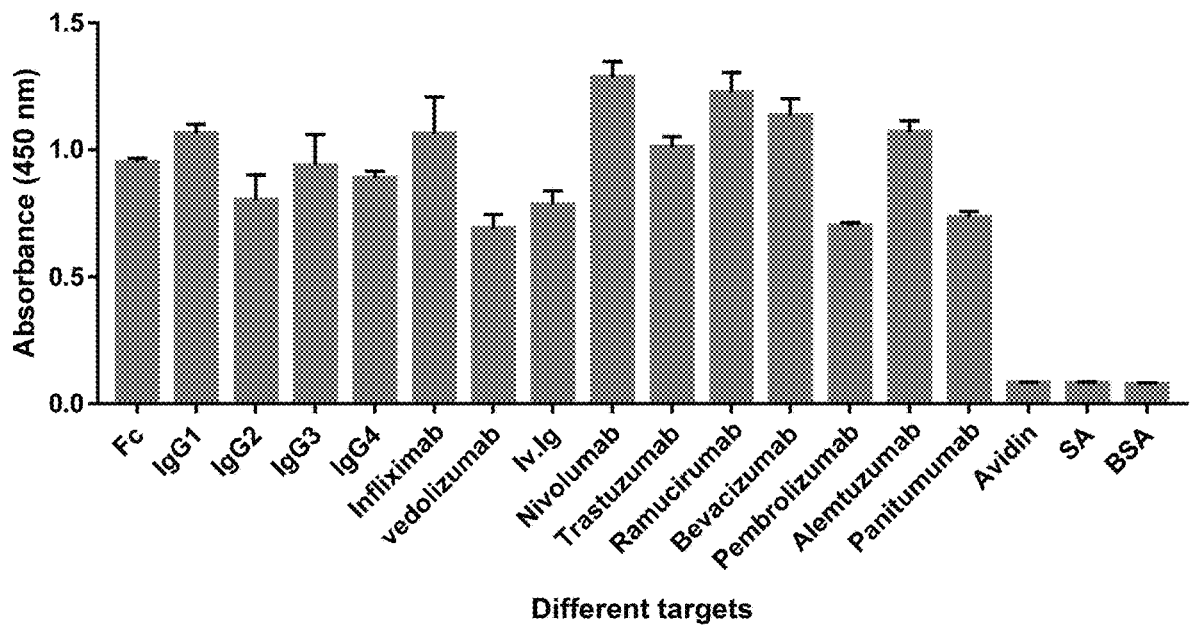

FIG. 5: Relative binding of the peptide with amino acid sequence identical to SEQ ID NO: 2 to human IgG Fc, human IgGs of different subclasses ($IgG_1$, $IgG_2$, $IgG_3$ and $IgG_4$) and a set of different therapeutic monoclonal antibodies as assessed by phage ELISA assay. BSA, avidin and streptavidin (SA) were used as negative controls. The peptide was displayed on phage particles as P3 fusion.

Figure 6:
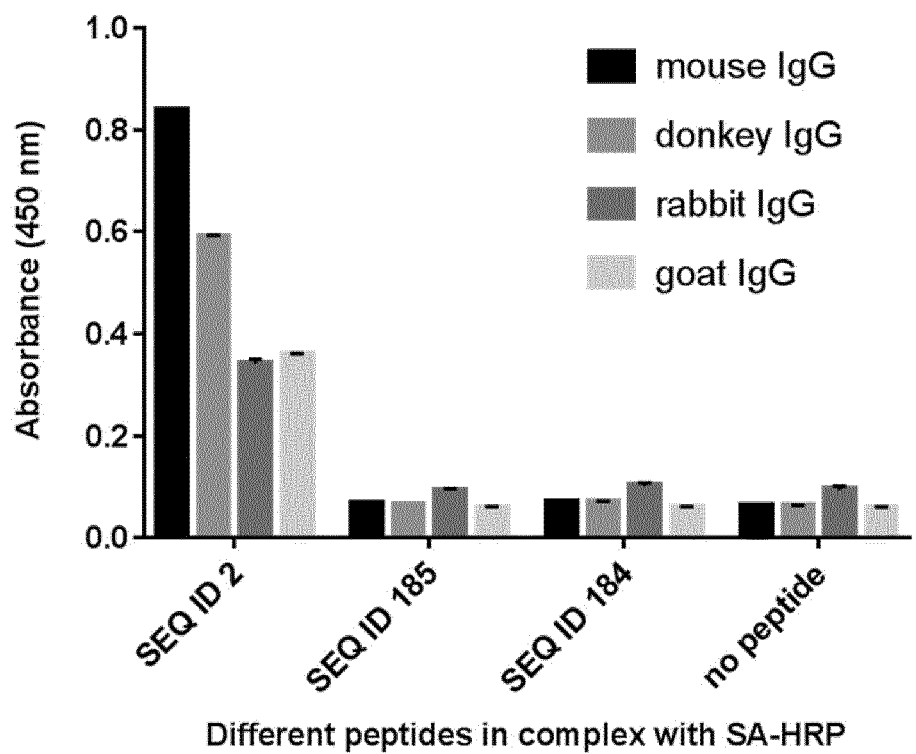

FIG. 6: Relative binding of complexes of synthetic peptide SEQ ID NO: 2 with C-terminal linker SEQ ID NO: 181 biotinylated at ε-amino group of residue K ($NH_2$-GSYWYQVWFGGGSR(K-ε-biotin)-$CONH_2$) and streptavidin (SA)-HRP conjugate, to IgGs of different species (mouse, donkey, rabbit and sheep). Two synthetic peptides, SEQ ID NO: 184 and SEQ ID NO: 185, with biotin attached via ε amino group of C-terminal lysine, represent control synthetic peptides with unrelated amino acids sequences. Peptides were complexed to streptavidin (SA)-HRP conjugate prior to contacting the IgG-coated microtiter plate wells. SA-HRP conjugate alone (i.e., not coupled to peptides, marked as no peptide) was used as a negative control.

Figure 7:
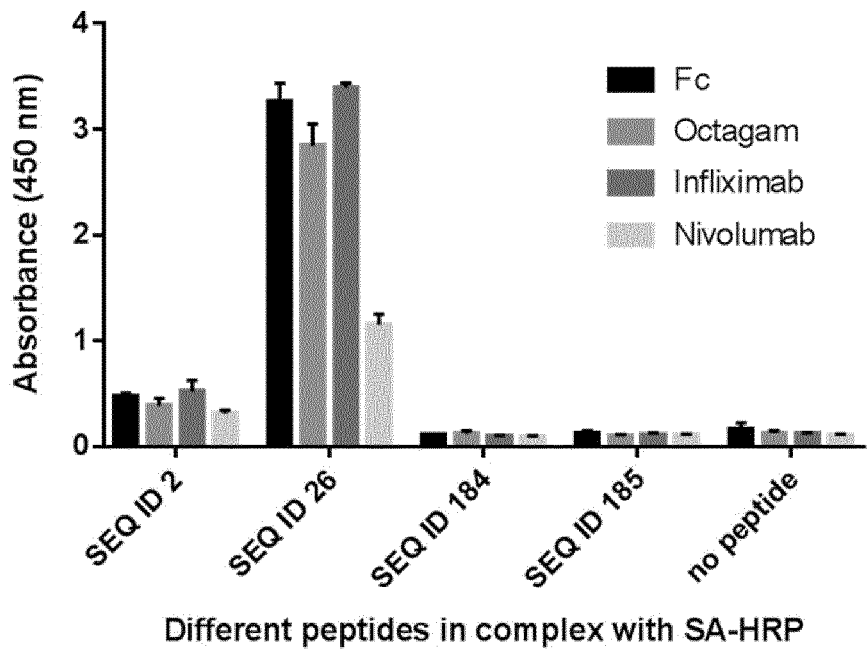

FIG. 7: Binding specificity and relative binding affinity of the Fc-specific synthetic peptides SEQ ID NO: 2, SEQ ID NO: 26 and SEQ ID NO: 30 with C-terminal linkers SEQ ID NO: 181 biotinylated at ε-amino group of residue K to human IgG Fc fragment, therapeutic monoclonal antibodies infliximab (recombinant chimeric $IgG_1$) and nivolumab (recombinant human $IgG_4$), and intravenous immunoglobulin. Two peptides SEQ ID NO: 184 and SEQ ID NO: 185 with biotin attached via ε-amino groupe of C-terminal lysine, represent two control synthetic peptides with unrelated amino acids sequences. Peptides were complexed to streptavidin (SA)-HRP conjugate prior to contacting the IgG-coated microtiter plate wells. SA-HRP conjugate alone (i.e., not coupled to peptides) was used as a negative control.

Figure 8:
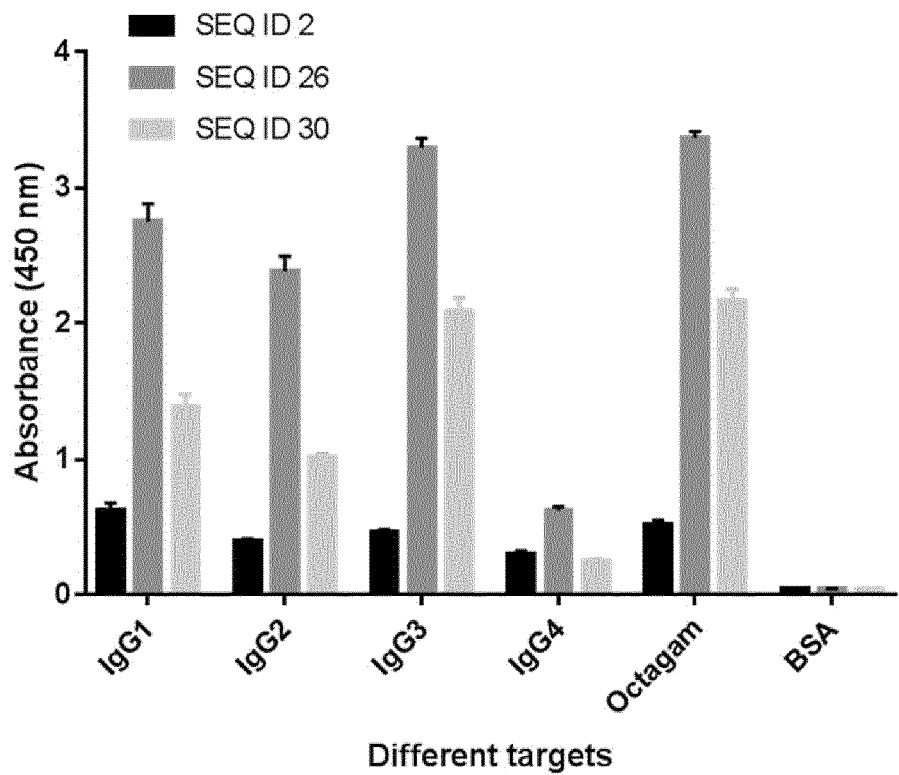

FIG. 8: Relative binding of complexes, comprised of different synthetic peptides SEQ ID NO: 2, SEQ ID NO: 26 and SEQ ID NO: 30 with C-terminal linkers SEQ ID NO: 181 biotinylated at ε-amino group of residue K and streptavidin (SA)-HRP conjugate, to human IgGs of different subclasses ($IgG_1$, $IgG_2$, $IgG_3$ and $IgG_4$) and a mixture thereof (intravenous immunoglobulin). BSA was used as a negative control.

Figure 9:
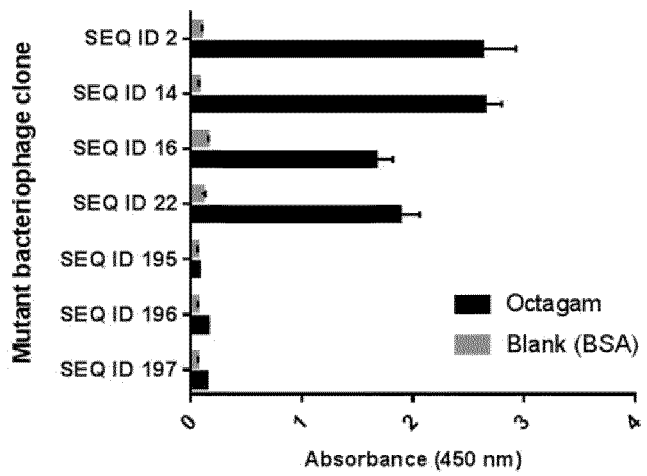
Figure 9:
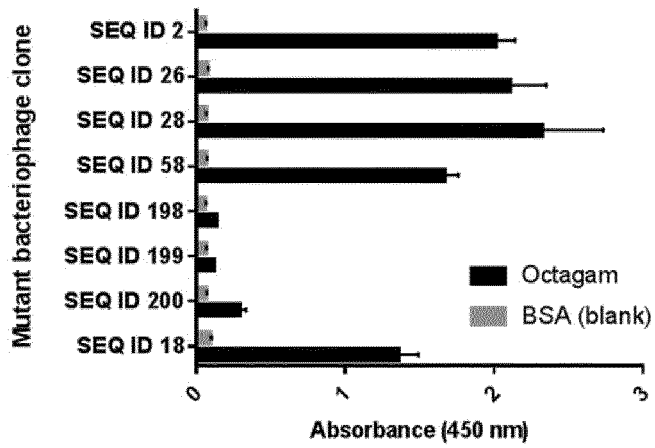

FIG. 9: Relative binding of different variants of peptides with amino acids identical to SEQ ID NO: 2 (section A) and SEQ ID NO: 26 (section B) with amino acid substitutions at different positions, to human IgG Fc fragment as assessed by phage ELISA assay. Individual variants were displayed on phage particles as P3 fusions.

Figure 10:
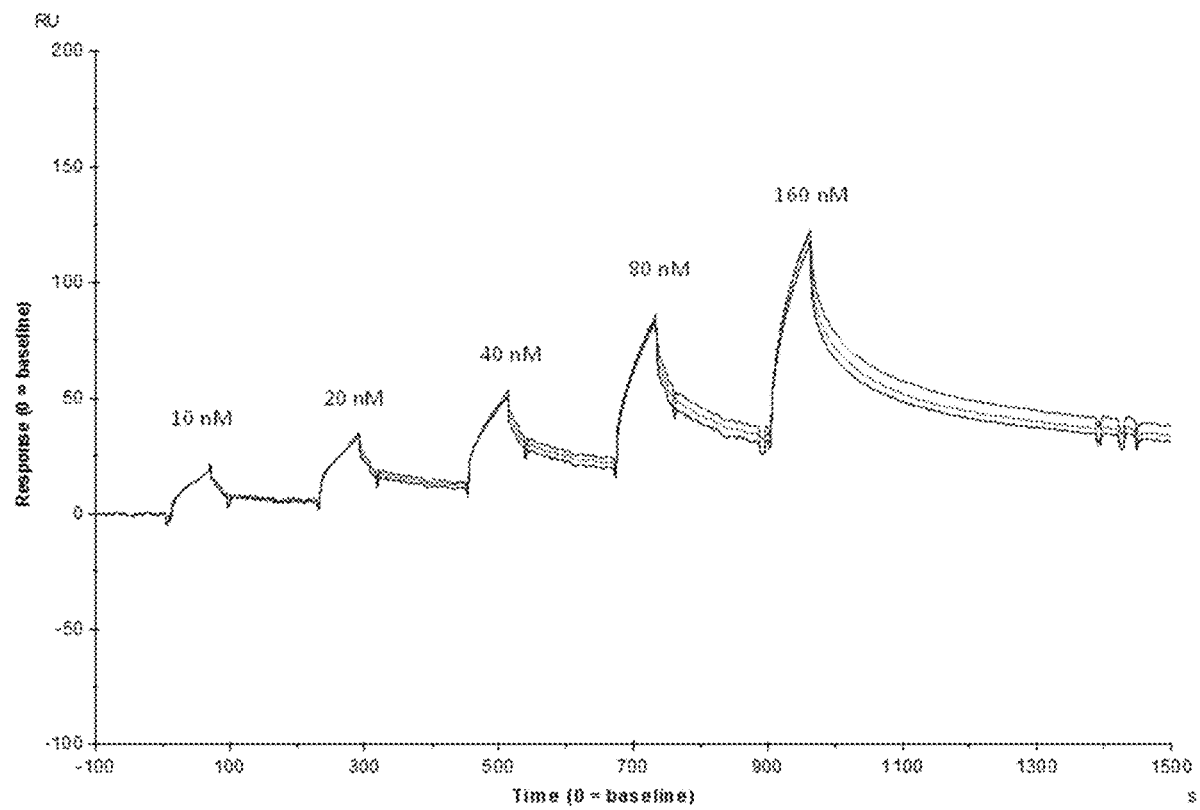

FIG. 10: Binding of the human IgG Fc fragment to synthetic peptide SEQ ID NO: 2 with C-terminal linker SEQ ID NO: 181 biotinylated at ε-amino group of residue K immobilized to surface plasmon resonance chip. Horizontal axis represent time (seconds) and vertical axis represent response units (RUs). The interaction was confirmed in three single-cycle kinetics measurements.

Figure 11:
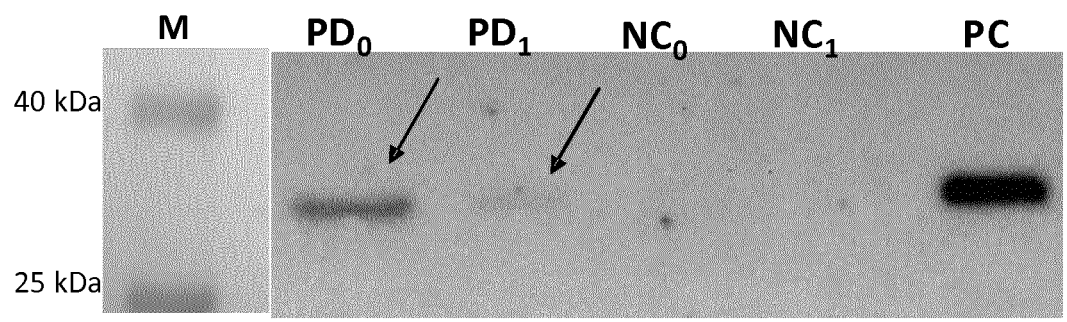

FIG. 11: Western blot analysis of a pull-down assay from DMEM medium spiked with human IgG Fc fragment using the synthetic peptide SEQ ID NO: 2 with C-terminal linker SEQ ID NO: 181 biotinylated at ε-amino group of residue K coupled to paramagnetic streptavidin beads. PD stands for pull-down experiment using peptide SEQ ID NO: 2-coated beads ($PD_0$, undiluted eluate; $PD_1$, 10-fold diluted eluate), NC stands for negative control (pull-down with uncoated beads); PC stands for positive control (Fc standard loaded directly on gel). The arrow indicates the band in pull down eluate which corresponds to the Fc fragment.

Figure 12:
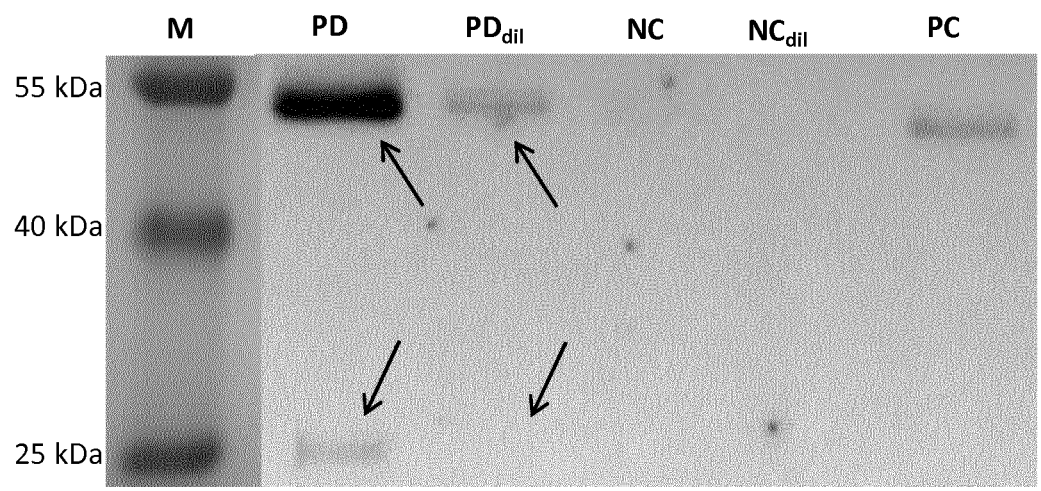

FIG. 12: Western blot analysis of a pull-down assay from human serum using the synthetic peptide SEQ ID NO: 2 with C-terminal linker SEQ ID NO: 181 biotinylated at ε-amino group of residue K coupled to paramagnetic streptavidin beads. PD denotes pull-down experiment using peptide SEQ ID NO: 2-coated beads ($PD_0$, undiluted eluate; $PD_{dil}$, 10-fold diluted eluate), NC denotes negative control (pull-down with uncoated beads; $NC_0$, undiluted control; $NC_{dil}$, 10-fold diluted control); SERUM represents diluted human serum directly loaded on gel as a positive control. The arrows indicate the bands corresponding to the heavy and light chains of human IgGs.

Figure 13:
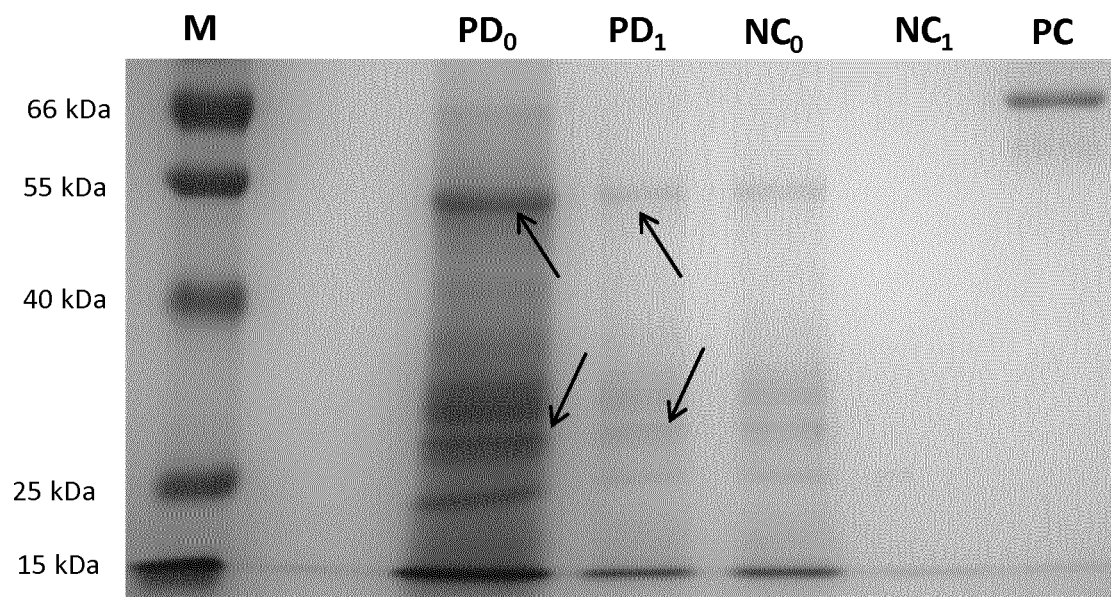

FIG. 13: The Coomassie stained gel after SDS-PAGE analysis of pull-down assay from human serum using the synthetic peptide SEQ ID NO: 2 with C-terminal linker SEQ ID NO: 181 biotinylated at ε-amino group of residue K coupled to streptavidin paramagnetic beads. PD stands for pull-down experiments with SEQ ID NO: 2 peptide-coated beads ($PD_0$, undiluted eluate; $PD_1$, 10-fold diluted eluate), NC stands for negative control (pull-down assay with uncoated beads); PC stands for positive control and represents diluted human serum directly loaded on the gel (only the band corresponding to serum albumin is seen).

Figure 14:
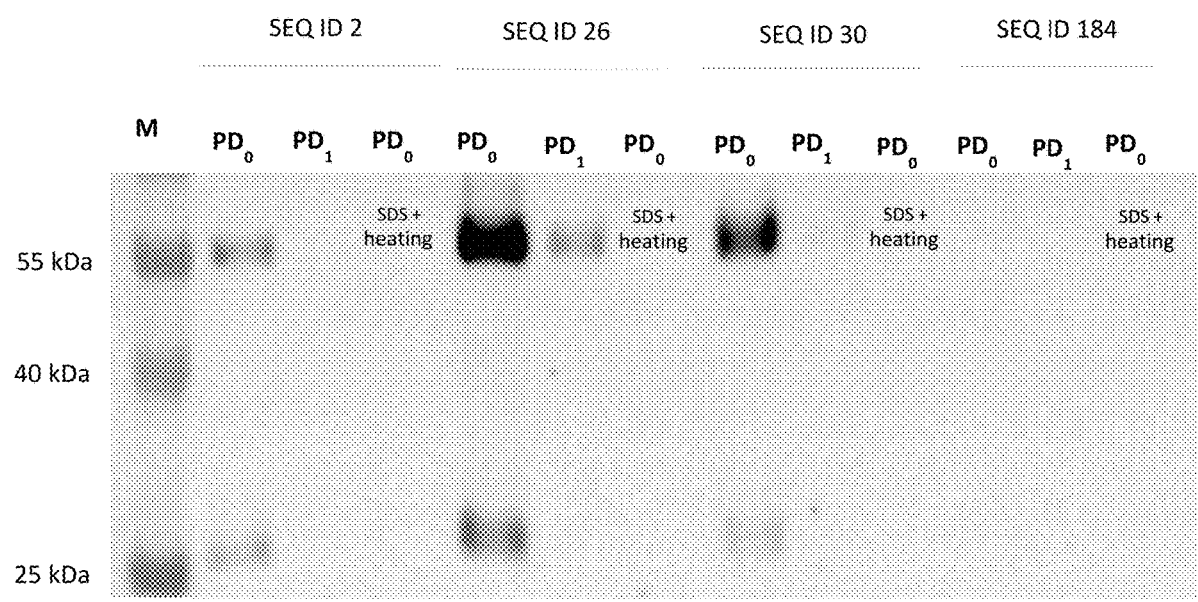

FIG. 14: Western blot analysis of pull-down assays from human serum using different synthetic peptides SEQ ID NO: 2, SEQ ID NO: 26 and SEQ ID NO: 30 with C-terminal linker SEQ ID NO: 181 biotinylated at ε-amino group of residue K coupled to streptavidin paramagnetic beads. PD represents pull-down experiments with individual peptide-coupled beads ($PD_0$, undiluted eluate; $PD_1$, 10-fold diluted eluate), SEQ ID NO: 184 represents pull-down experiments using beads coupled with a control peptide with unrelated amino acid sequence. $PD_0$ (SDS+heating) represent the residual bound fraction eluted by the addition of SDS and boiling the beads for 4 minutes after preceding acidic elution.

Figure 15:
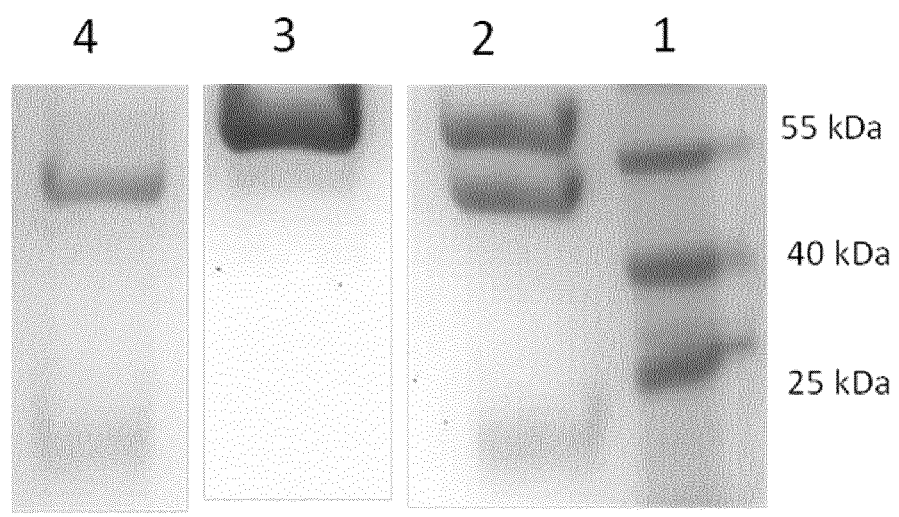

FIG. 15: Chromatographic isolation of IgGs from spiked PBS on the peptide with amino acid sequence identical to SEQ ID NO: 1-based affinity column. Human IgGs and BSA was spiked into PBS with 1 M NaCl at pH 7.4 in ration 1:1 and the sample was loaded onto the column. The column was washed with PBS with 1 M NaCl at pH 7.4 and eluted with glycine hydrochloride buffer pH 2.5. Coomassie blue stained SDS-PAGE of separation denoted in lane 1: molecular marker; lane 2:1:10 dilution of loading material; line 3 correspond to flow through; line 4 correspond to eluted human IgG with 0.1 M Glycine HCl, pH 2.5. All samples were analysed under reducing conditions.

E. DETAILED DESCRIPTION OF THE PREFERRED EMBODIMENTS

Unless defined otherwise, all technical and scientific terms used herein possess the same meaning as it is commonly known to experts in the field of invention. The terminology to be used in the description of the invention has the purpose of description of a particular segment of the invention and has no intention of limiting the invention. In the description of the invention and in the claims, the description is in the singular form, but also includes the plural form, what is not specifically highlighted for ease of understanding.

1. Definitions

"Antibody" or "antibodies" as used herein refer to all types of immunoglobulins, including IgG, IgM, IgA, IgD, and IgE. The term "immunoglobulin" includes the subtypes of these immunoglobulins, such as $IgG_1$, $IgG_2$, $IgG_3$, $IgG_4$, etc. Of these immunoglobulins, IgM and IgG are preferred, and IgG is particularly preferred. The antibodies may be of any species of origin, including (for example) mouse, rat, rabbit, horse, donkey, sheep or human, or may be recombinant chimeric, humanized or bispecific antibodies. Antibodies can be monoclonal or polyclonal. The term "polyclonal antibody" denotes a mixture of different antibody molecules which react with more than one immunogenic determinant of an antigen. The term "monoclonal antibody" as used herein refers to an antibody obtained from a population of substantially homogeneous antibodies, i.e., the individual antibodies comprising the population are identical. Monoclonal antibodies are highly specific, being directed against a single antigenic site. In addition to their specificity, the monoclonal antibodies are advantageous in that they can be synthesized by hybridoma culture, uncontaminated by other immunoglobulins. Both "chimeric antibodies" and "humanized antibodies" refer to antibodies that combine regions from more than one species. For example, "chimeric antibodies" traditionally comprise variable region(s) from a mouse (or rat, in some cases) and the constant region(s) from a human. "Humanized antibodies" generally refers to non-human antibodies that have had the variable-domain framework regions swapped for sequences found in human antibodies. Generally, in a humanized antibody, the entire antibody, except the CDRs, is encoded by a polynucleotide of human origin or is identical to such an antibody except within its CDRs. The CDRs, some or all of which are encoded by nucleic acids originating in a non-human organism, are grafted into the beta-sheet framework of a human antibody variable region to create an antibody, the specificity of which is determined by the engrafted CDRs. The humanized antibody optimally also will comprise at least a portion of an immunoglobulin constant region, typically that of a human immunoglobulin, and thus will typically comprise a human Fc region.

By "Fc fusion" as used herein is meant an Fc fragment of antibody wherein one or more peptides or proteins is operably linked to an Fc region or derivative thereof. Fc fusion is herein meant to be synonymous with the terms "immunoadhesin", "Ig fusion", "Ig chimera". An Fc fusion combines the Fc region of an immunoglobulin with a fusion partner, which in general can be any protein, polypeptide, peptide, or a small molecule. The role of the non-Fc part of an Fc fusion, i.e., the fusion partner, is often but not always to mediate target binding, and thus it is functionally analogous to the variable regions of an antibody. A variety of linkers, defined and described below, may be used to covalently link an Fc region to a fusion partner to generate an Fc fusion.

"Amino acid" and "amino acid identity" as used herein refers to one of the 20 proteinogenic amino acids or any nonconventional analogues that may be present at a specific, defined peptide, ligand or protein position. The side chain may be in either the L or the D configuration. The term "nonconventional" amino acids refer to amino acids other than conventional amino acids (i.e., other than proteinogenic). Examples of nonconventional amino acids include, but are not limited to: β-alanine, 3-pyridylalanine, 4-hydroxyproline, 0-phosphoserine, N-methylglycine (also known as sarcosine), N-acetylserine, N-formylmethionine, 3-methylhistidine, 5-hydroxylysine, nor-leucine, 1-naphthylalanine (1-nal), 2-naphthylalanine (2-nal), homoserine methylether (Hsm), N-acetylglycine, and other similar amino acids and imino acids.

By "residue" as used herein is meant a position in a protein or peptide and its associated amino acid identity. For example, glutamine 6 (also referred to as Gln6, also referred to as Q6) is a glutamine residue on position 6 in the Fc-binding peptide.

By "position" as used herein is meant a location in the sequence of a protein or peptide. Positions may be numbered sequentially. For example, position 6 is a position of the sixth consecutive residue (counting from N- to C-terminus) in the Fc-binding peptide. Corresponding positions are determined as outlined below, generally through sequence or structural alignment with other protein or peptide sequences.

"Sequence" means the linear order in which monomers occur in a polymer, for example, the order of amino acids in a polypeptide or the order of nucleotides in a polynucleotide.

"Peptide" is defined herein as an organic compound comprising a chain of at least two amino acids covalently linked by a peptide bond. In general, peptides include proteins, polypeptides and oligopeptides. By "single protein" or "single peptide" as used herein is meant a protein or peptide that contains only a contiguous sequence of amino acids, i.e. wherein all amino acid residues of the protein or peptide are linked via peptide bonds. Thus, non-covalently linked peptides and peptides linked via covalent bonds other than peptide bonds, for example via disulfide bonds or post-translational modifications, are not herein considered single peptides. Peptide sequences are provided using the single-letter IUPAC amino acid code.

"Polynucleotide" is defined herein as an organic compound composed of at least 6 covalently bonded nucleotide monomers. DNA (deoxyribonucleic acid) and RNA (ribonucleic acid) are examples of polynucleotides.

"Composition" as used herein refers to a liquid containing at least one immunoglobulin, which is sought to be purified from other substances also present. Compositions are often complex mixtures or solutions containing many biological molecules such as proteins, antibodies, hormones and viruses as well as small molecules such as salts, sugars, and lipids. Examples of compositions that may contain immunoglobulins of interest include, but are not limited to, blood or blood plasma, plasma fractions, ascites fluid, aqueous cell culture and milk.

"Label" or "detectable group" as used herein may be any suitable label or detectable group which allow detection by spectroscopic, photochemical, biochemical, immunochemical, electrical, optical or chemical means including but not limited to biotin, fluorophores and antigens. Labels useful in the present invention include biotin for staining with labelled avidin or streptavidin conjugate, magnetic beads (e.g., Dynabeads™), quantum dots (e.g., Qdots®), fluorescent dyes (e.g., fluorescein-isothiocyanate [FITC]), enzymes (e.g., hydrolases, particularly phosphatases such as alkaline phosphatase, or oxidoreductases, particularly peroxidases such as horseradish peroxidase, and the like), substrates, inhibitors, chemiluminescent groups, chromogenic agents such as colloidal Coomassie.

As used herein, "drug" is an agent or a substance that has measurable specified or desired biological or pharmacological effect when administered to a subject in a significant or effective amount. These terms of art are well-known in the pharmaceutical and medicinal arts.

By "diagnostic agent" as used herein may be a protein, nucleic acid molecule, compound, small molecule, organic compound, inorganic compound, or any other molecule used to examine the body in order to detect impairment of its normal functions.

By "linker", "linker sequence", "spacer", "tethering sequence" or grammatical equivalents thereof, herein is meant a molecule or group of molecules (such as a monomer or polymer, respectively) that connects two molecules and often serves to place the two molecules in a preferred configuration. A number of strategies may be used to covalently link molecules together. These include, but are not limited to polypeptide linkages between N- and C-termini of proteins or protein domains, linkage via disulfide bonds, and linkage via chemical cross-linking reagents. In one aspect of this embodiment, the linker is a peptide bond, generated by recombinant techniques or peptide synthesis. Choosing a suitable linker for a specific case where peptide chains are to be connected to different conjugate or fusion partner depends on various parameters, including but not limited to the nature of the two peptide chains (e.g., whether they naturally oligomerize), the distance between the N- and the C-termini to be connected if known, and/or the stability of the linker towards proteolysis and oxidation. Furthermore, the linker may contain amino acid residues that provide flexibility. Thus, the linker peptide may predominantly include the following amino acid residues: Gly, Ser, Ala, or Thr. The linker peptide should have a length that is adequate to link two molecules in such a way that they assume the correct conformation relative to one another so that they retain the desired activity. Suitable lengths for this purpose include at least one and not more than 50 amino acid residues. Preferably, the linker is from about 1 to 20 amino acids in length, with linkers of 1 to 10 amino acids in length being most preferred. In addition, the amino acid residues selected for inclusion in the linker peptide should exhibit properties that do not interfere significantly with the activity of the peptide. Thus, the linker peptide on the whole should not exhibit a charge that would be inconsistent with the activity of the polypeptide, or interfere with internal folding, or form bonds or other interactions with amino acid residues in one or more of the monomers that would seriously impede the binding of receptor monomer domains. Useful linkers include glycine-serine polymers (including, for example, (GS)n, (GGGSRK)n (SEQ ID NO:181), (GGGSK)n (SEQ ID NO:182), (GGGSKK)n (SEQ ID NO:183), (GGDDK)n (SEQ ID NO:205), and (GGDSK)n (SEQ ID NO:206), where R, D and K serve for increasing solubility and n is an integer of 1, 2, 3, 4 or 5), glycine-alanine polymers, alanine-serine polymers, and a large variety of other flexible linkers, as will be appreciated by those in the art.

The linker may be cleavable, for example, and not limited to, to facilitate release of the conjugated cytotoxic drug in the cell. Alternatively, a variety of nonproteinaceous polymers, including but not limited to polyethylene glycol (PEG), polypropylene glycol, polyoxyalkylenes, or copolymers of polyethylene glycol and polypropylene glycol, may find use as linkers for connecting the Fc-binding ligands of the present invention to a conjugate partner to generate a non-covalent complex with Fc region of antibody molecule.

"Duration enhancing moiety" as used herein refers to a moiety to which ligand is covalently attached. Attachments of such moieties affect ligand pharmacokinetics; more specifically they increase ligand's metabolic stability and plasma half-life; in turn metabolic stability and plasma half-life of the ligand-immunoglobulin and ligand-Fc fusion protein complex are increased as well. Such duration enchaining moieties are, but not limited to, water-soluble polymers, such as polyethylene glycol (PEG), peptide and glycans, or fatty acids. The number of duration enhancing moieties attached may vary; for example, one, two, three, or more identical or different duration enhancing moieties may be attached to the ligand of the invention.

As used herein, the term "multimer" and "oligomer" refers to multimeric forms of the ligands of interest. A "multimer" may be made by linking multiple copies (two or more) of a ligand to each other. The multimer of the invention may be trimers, tetramers, pentamer, or other higher order structures.

"Dendrimer" is a repetitively branched molecule, typically symmetric around the core. Peptide dendrimers are radial or wedge-like branched macromolecules consisting of a peptidyl branching core and/or covalently attached surface functional units.

"Conjugate partner" is a molecule, such as peptide, protein, protein fragment, a small-molecular weight molecule or a linker as defined herein, that is coupled to the Fc-binding ligand via non-peptide covalent bond. "Fusion partner" is a peptide, protein, a protein fragment or a proteinaceous linker as defined herein that is coupled to the Fc-binding peptide via peptide bond.

"Ligand" as used herein refers to a molecule or group of molecules that bind to one or more specific sites of a partner molecule. Herein, the ligand binds to the Fc region.

"Solid support", "solid phase support" or "matrix" as used herein refers to an inert material or molecule to which a ligand may be bound or coupled, either directly or indirectly through a linking group. The solid phase support is suitable for use in pull down assay, column chromatography or other types of purification.

By "amino acid modification" herein is meant an amino acid substitution, insertion, and/or deletion in a peptide sequence. By "amino acid substitution" or "substitution" herein is meant the replacement of an amino acid at a particular position in a parent peptide sequence with another amino acid. For example, the substitution Q6A refers to the substitution of glutamine for alanine at position 6. Modification also includes additions of protective or capping groups on reactive moieties, and other changes that do not adversely destroy the binding affinity of the peptide compound. An "amino terminal capping group" of a peptide compound described herein is any chemical compound or moiety that is linked, preferably covalently, to the amino terminal amino acid residue of a peptide compound. An amino terminal capping group may be useful to inhibit or prevent intramolecular cyclization or intermolecular polymerization, to mask the positive charge of the terminal amino group, to prevent degradation of the peptide compound, to provide specific chemical reactivity, or to provide a combination of these properties. Examples of amino terminal capping groups of peptide compounds useful in the invention include, but are not limited to, acetyl, acryl, allyloxycarbonyl, benzoyl, tert-butyloxycarbonyl, 9-fluorenylmethyloxycarbonyl, bromoacetyl, benzyloxycarbonyl, dansyl, formyl, maleimide, N-hydroxysuccinimide, iodoacetyl, epoxy, hydrazide, cyano or any acyl groups and linkers as defined herein. A "carboxy terminal capping group" of a peptide compound described herein is any chemical compound or moiety that is linked, preferably covalently, to the carboxy terminal amino acid residue of the peptide compound. A carboxy terminal capping group may be useful to inhibit or prevent intramolecular cyclization or intermolecular polymerization, to mask the negative charge of the terminal carboxyl group, to prevent degradation of the peptide compound, to provide specific chemical reactivity, or to provide a combination of these properties. Carboxy terminal capping groups that are particularly useful in the peptide compounds described herein include primary or secondary amines that are linked by an amide bond to the α-carboxyl group of the carboxy terminal amino acid of the peptide compound and can serve as linkers as defined herein. Additional carboxy terminal groups include, but are not limited to, 7-amino-4-methylcoumarin, 7-amino-4-trifluoromethylcoumarin, tert-butyl, p-nitroanilide, and maleimide.

The term "peptidomimetic" or "peptide mimetic" refers to any synthetic organic molecule that has a three-dimensional structure designed to be substantially similar to a three-dimensional structure of a peptide. Examples of peptidomimetics are, but not limited to, peptoids (polymers of N-substituted 2-aminoacetic acids connected with peptide bonds, i.e., peptide analogues with amino acid side chains relocated from the alpha C-atom to adjacent alpha nitrogen atom of the peptide backbone), peptides containing non-standard (i.e., non-proteinogenic) amino acids other than D-amino acids, or conformationally constrained (e.g., cyclized) versions thereof.

"Retro-inverso" modification of naturally occurring polypeptides involves the synthetic assemblage of amino acids with α-carbon stereochemistry opposite to that of the corresponding L-amino acids, i.e. D- or D-allo-amino acids, in reverse order with respect to the native peptide sequence. A "retro-inverso analogue" thus has reversed termini and reversed direction of peptide bonds while approximately maintaining the topology of the side chains as in the native peptide sequence. Accordingly, a "retro inverso analogue" of the ligand of the invention may have the following general structure: $Z-X^9-X^8-X^7-X^6-X^5-X^4-X^3-X^2-X^1-U$, with Z and U being as defined herein, and $X^1$ to $X^9$ being as defined herein, except that they are in the D- or D-allo form.

"Transformant" as used herein means any cell including, but not limited to, bacterial cell, fungal cell, yeast cell, insect cell, mammalian cell, or plant cell into which a foreign DNA, such as the polynucleotide or vector of the present invention has been introduced By "Fc region" as used herein is meant the protein comprising of two identical protein fragments, derived from the second and third constant domains of the antibody's two heavy chains. Fc region generally refers to the last two constant immunoglobulin domains of IgA, IgD, and IgG heavy chains, and the last three constant region immunoglobulin domains of IgE and IgM. Fc region may also include part or the entire flexible hinge N-terminal to these domains. For IgG, Fc region comprises immunoglobulin domains Cgamma2 and Cgamma3 (Cγ2 and Cγ3) and the lower part of the hinge between Cgamma1 (Cγ1) and Cγ2.

By "parent peptide" or "parent protein" as used herein is meant a peptide that is subsequently modified to generate a variant. Said parent peptide or protein may be a naturally occurring peptide, or a variant or engineered version of a naturally occurring peptide. Parent peptide may refer to the peptide itself, compositions that comprise the parent peptide, or the corresponding amino acid sequence. Accordingly, by "parent peptide" as used herein is meant a peptide that is modified to generate a variant.

By "variant peptide", "protein variant", "peptide variant", as used herein is meant a peptide sequence that differs from that of a parent peptide sequence by virtue of at least one amino acid modification. Variant peptide may refer to the peptide itself, a composition comprising the peptide, or the corresponding amino acid sequence.

The original (unmodified) peptides as disclosed herein can be modified by the substitution of one or more residues at different, possibly selective, sites within the peptide chain, if not otherwise stated. Such substitutions may be of a "conservative" nature, wherein a substituted amino acid has similar structural and/or chemical properties. Exemplary, suitable conservative amino acid substitutions may be replaced by an amino acid of similar structure and characteristics, shown in Table 1 under the heading "Exemplary substitutions". Even more conservative would be replacement of amino acids of the same or similar size and chemical nature, such as where leucine is replaced by isoleucine, shown in Table 1 under the heading "Preferred substitutions".

TABLE 1

Examples of conservative amino acid substitutions.

| Original Residue | Exemplary Substitutions | Preferred substitutions |
| --- | --- | --- |
| Ala (A) | Val, Leu, Ile | Val |
| Arg (R) | Lys, His | Lys |
| Asn (N) | Gln, His, Asp, Lys, Arg | Gln |
| Asp (D) | Glu, Asn | Glu |
| Cys (C) | Ser, Ala | Ser |
| Gln (Q) | Asn, Glu | Asn |
| Glu (E) | Asp, Gln | Asp |
| Gly (G) | Ala | Ala |
| His (H) | Asn, Gln, Lys, Arg | Arg |
| Ile (I) | Leu, Val, Met, Ala, Phe, Norleucine | Leu |
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Trp, Leu, Val, Ile, Ala, Tyr | Tyr |
| Pro (P) | Ala | Ala |
| Ser (S) | Thr | Thr |
| Thr (T) | Val, Ser | Ser |
| Trp (W) | Tyr, Phe | Tyr |

TABLE 1-continued

Examples of conservative amino acid substitutions.

| Original Residue | Exemplary Substitutions | Preferred substitutions |
|---|---|---|
| Tyr (Y) | Trp, Phe, Thr, Ser | Phe |
| Val (V) | Ile, Leu, Met, Phe, Ala, Norleucine | Leu |

In studies of sequence variations in families of naturally occurring homologous proteins, certain amino acid substitutions are more often tolerated than others, and these are often show correlation with similarities in size, charge, polarity, and hydrophobicity between the original amino acid and its replacement, and such is the basis for defining "conservative substitutions." Conservative substitutions are herein defined as exchanges within one of the following five groups: Group 1-small aliphatic, nonpolar or slightly polar residues (Ala, Ser, Thr, Pro, Gly); Group 2-polar, negatively charged residues and their amides (Asp, Asn, Glu, Gln); Group 3-polar, positively charged residues (His, Arg, Lys); Group 4-large, aliphatic, nonpolar residues (Met, Leu, Ile, Val, Cys); and Group 5-large, aromatic residues (Phe, Tyr, Trp).

Less conservative substitutions might involve the replacement of one amino acid by another that has similar characteristics but is somewhat different in size, such as replacement of an alanine by an isoleucine residue. Highly nonconservative replacements might involve substituting an acidic amino acid for one that is polar, or even for one that is basic in character. Such "radical" substitutions cannot, however, be dismissed as potentially ineffective since chemical effects are not totally predictable and radical substitutions might well give rise to serendipitous effects not otherwise predictable from simple chemical principles.

Such substitutions may involve structures other than the common L-amino acids. Thus, D-amino acids might be substituted for the L-amino acids and yet still be encompassed by the disclosure herein. In addition, non-standard amino acids (i.e., other than the common naturally occurring proteinogenic amino acids) may also be used for substitution purposes to produce similar peptides according to the present invention. If substitutions at more than one position are found to result in a peptide with substantially equivalent or greater binding affinity and/or selectivity, then combinations of those substitutions can be tested to determine if the combined substitutions result in additive or synergistic effects on the affinity/binding selectivity of the peptide.

The peptide compounds of the invention also serve as structural models for non-peptidic compounds with similar biological activity. Those skilled in art recognize that a variety of techniques are available for constructing compounds with the same or similar desired biological activity as the lead peptide. These techniques include replacing the peptide backbone with a backbone composed of phosphonates, amidates, carbamates, sulphonamides, secondary amines and N-methylamino acids.

In accordance with the present invention, the term "percent identity" or "% identity", when referring to a sequence, means that a sequence is compared to a claimed or described sequence after alignment of the sequence to be compared (the "Compared Sequence") with the described or claimed sequence (the "Reference Sequence"). The percent identity is then determined according to the following formula:

Percent identity=$100[1-(C/R)]$ wherein C is the number of differences between the Reference Sequence and the Compared Sequence over the length of alignment between the Reference Sequence and the Compared Sequence, wherein
i. each amino acid in the Reference Sequence that does not have a corresponding aligned amino acid in the Compared Sequence and
ii. each gap in the Reference Sequence and
iii. each aligned amino acid in the Reference Sequence that is different from an aligned amino acid in the Compared Sequence, constitutes a difference and
iv. the alignment has to start at position 1 of the aligned sequences; and R is the number of amino acids in the Reference Sequence over the length of the alignment with the Compared Sequence with any gap created in the Reference Sequence also being counted as an amino acid.

If an alignment exists between the Compared Sequence and the Reference Sequence for which the percent identity as calculated above is about equal to or greater than a specified minimum Percent Identity then the Compared Sequence has the specified minimum percent identity to the Reference Sequence even though alignments may exist in which the herein above calculated percent identity is less than the specified percent identity.

The term "substantial sequence identity" between peptide sequences refers to peptide comprising a sequence that has at least 60% sequence identity, such as at least 70%, at least 75%, at least 80%, at least 85%, at least 90%, at least 91%, at least 92%, at least 93%, at least 94%, at least 95%, at least 96%, at least 97%, at least 98% or at least 99%.

As mentioned above, the present invention thus provides a ligand comprising an amino acid sequence that is selected from the group of consisting of SEQ ID NO: 1 to SEQ ID NO: 173, or a variant thereof which has at least 60% sequence identity with any one of SEQ ID NO: 1 to SEQ ID NO: 173, or a variant thereof that will bind to Fc fragment of antibody with said ligand. The ligands of the invention have the ability to bind to Fc fragment of the antibodies.

"Binding affinity" refers to a property of a ligand which may be tested, e.g. by the use of surface plasmon resonance technology such as in a Biacore® instrument, and reflects a strength of binding or the stability of the formed complex. Binding affinity may be tested in an experiment wherein the ligand to be tested is immobilized on a sensor chip of the instrument, and a sample containing human Fc fragment is passed over the chip. The skilled person may then interpret the sensograms obtained to establish at least a qualitative measurement of the ligands' binding affinity for human Fc region. If a quantitative measure is sought, for example with the purpose to determine a certain or apparent $K_D$ value for the interaction, it is again possible to use surface plasmon resonance methods. Binding values may for example be defined using a Biacore® X100 instrument (Biacore). The ligand to be tested may be immobilized on a sensor chip of the instrument, and samples representing serially diluted human Fc fragment injected in a random order. Apparent $K_D$ values may then be calculated from the results after fitting the curves to the the 1:2 bivalent binding model, for example, using the BIAevaluation software provided by the instrument manufacturer. Binding affinity for human Fc fragment may also be tested by conventional methods.

A "hapten" herein is defined as a small molecule which by itself cannot stimulate antibody production, but can stimulate antibody production when coupled to an immunogenic carrier. Hence, antibodies can be produced that specifically recognize and bind such small molecules.

2. Ligands

The immunoglobulin binding ligand according to the present invention is a ligand with a short chain length, containing a sequence of amino acids or an analogous sequence. Written from amino terminus to carboxy terminus, the ligand of the present invention has the general structure I:

$Z\text{-}X^1\text{-}X^2\text{-}X^3\text{-}X^4\text{-}X^5\text{-}X^6\text{-}X^7\text{-}X^8\text{-}X^9\text{-}U$ (Structure I)

where $X^1$ may or may not be present, but if present it can be any amino acid, preferably G; $X^2$ may or may not be present, but if present it is a hydrophilic (polar) amino acid, preferably S, T, C, N or K; $X^3$ is a hydrophobic, aromatic amino acid, preferentially Y; $X^4$ is a hydrophobic, aromatic amino acid, preferentially W; $X^5$ is a hydrophobic, aromatic amino acid, preferentially Y; $X^6$ can be any amino acid but preferably is one bearing a negative charge (for example, D or E) or A or K or Q, but preferentially is D; $X^7$ can be any amino acid but is preferably hydrophobic, aliphatic amino acid (for example V) or K; $X^8$ is a hydrophobic, aromatic amino acid, preferentially W; and $X^9$ is a hydrophobic, aromatic amino acid, preferentially F; Z is a hydrogen atom replacing the N-terminal amino group or an N-terminal amino group, or it is a capping group or a linker bound either to the N-terminal amino group or directly to the alpha C-atom of the N-terminal residue; and U is a hydrogen atom replacing the C-terminal carboxyl group or a C-terminal carboxyl group, or is a linker or capping group bound either to the C-terminal carbonyl group or directly to the alpha C-atom of the C-terminal residue.

According to some embodiments, $X^1$ is not present.
According to some embodiments, $X^1$ is present.
According to some embodiments, $X^1$ is G or A.
According to some embodiments, $X^1$ is G.
According to some embodiments, $X^2$ is not present.
According to some embodiments, the following proviso applies: if $X^1$ is present and $X^2$ is not present, then $X^1$ is not D-Phe.
According to some embodiments, the following proviso applies: if $X^1$ is present and $X^2$ is not present, then $X^1$ is not F.
According to some embodiments, $X^2$ is present.
According to some embodiments, $X^2$ is S, T, C, N or K.
According to some embodiments, $X^2$ is S.
According to some embodiments, $X^2$ is T.
According to some embodiments, $X^2$ is C.
According to some embodiments, $X^2$ is N.
According to some embodiments, $X^2$ is K.
According to some embodiments, $X^3$ is Y, W or F.
According to some embodiments, $X^3$ is Y.
According to some embodiments, $X^3$ is W.
According to some embodiments, $X^3$ is F.
According to some embodiments, $X^4$ is W, Y or F.
According to some embodiments, $X^4$ is W.
According to some embodiments, $X^4$ is Y.
According to some embodiments, $X^4$ is F.
According to some embodiments, $X^5$ is Y, W or F.
According to some embodiments, $X^5$ is Y.
According to some embodiments, $X^5$ is W.
According to some embodiments, $X^5$ is F.
According to some embodiments, $X^6$ is an amino acid bearing a negative charge.
According to some embodiments, $X^6$ is A, D, E, N, Q or K.
According to some embodiments, $X^6$ is A.
According to some embodiments, $X^6$ is D.
According to some embodiments, $X^6$ is E.
According to some embodiments, $X^6$ is N.
According to some embodiments, $X^6$ is Q.
According to some embodiments, $X^6$ is K.
According to some embodiments, $X^7$ is a small hydrophobic amino acid.
According to some embodiments, $X^7$ is V, A, K, C, I, L or M.
According to some embodiments, $X^7$ is A.
According to some embodiments, $X^7$ is V.
According to some embodiments, $X^7$ is C.
According to some embodiments, $X^7$ is K.
According to some embodiments, $X^7$ is I.
According to some embodiments, $X^7$ is L.
According to some embodiments, $X^7$ is M.
According to some embodiments, $X^8$ is W, Y or F.
According to some embodiments, $X^8$ is W.
According to some embodiments, $X^8$ is Y.
According to some embodiments, $X^8$ is F.
According to some embodiments, $X^9$ is F, W or Y.
According to some embodiments, $X^9$ is F.
According to some embodiments, $X^9$ is W.
According to some embodiments, $X^9$ is Y.
According to some embodiments, Z is a hydrogen atom replacing the N-terminal amino group.
According to some embodiments, Z is an N-terminal amino group.
According to some embodiments, Z is a linker or a capping group, bound either to the N-terminal amino group or directly to the alpha C-atom of the N-terminal residue.
According to some embodiments, Z is a linker, bound either to the N-terminal amino group or directly to the alpha C-atom of the N-terminal residue.
According to some embodiments, Z is a capping group, bound either to the N-terminal amino group or directly to the alpha C-atom of the N-terminal residue.
According to some embodiments, U is a hydrogen atom replacing the C-terminal carboxyl group.
According to some embodiments, U is a C-terminal carboxyl group.
According to some embodiments, U is a linker or a capping group, bound either to the C-terminal carbonyl group or directly to the alpha C-atom of the C-terminal residue.
According to some embodiments, U is a linker, bound either to the C-terminal carbonyl group or directly to the alpha C-atom of the C-terminal residue.
According to some embodiments, U is a capping group, bound either to the C-terminal carbonyl group or directly to the alpha C-atom of the C-terminal residue.

The amino acids of said ligand may be in L-form (L-enantiomer), D-form (D-enantiomer), D-form with reverted order (i.e., retro-inverso peptide), combination of both enantiomers or in the form of alpha N-substituted glycine residues forming the corresponding peptoid derivative.

The ligand of the present invention may also be in the form of peptidomimetics containing the phosphonate, amidate, carbamate ester or sulphonamide backbone linkages replacing the peptide backbone but retaining the sequences of side chains of the present invention. (The single letter code for amino acids is A (Ala), C (Cys), D (Asp), E (Glu), F (Phe), G (Gly), H (His), I (Ile), K (Lys), L (Leu), M (Met), N (Asn), P (Pro), Q (Gln), R (Arg), S (Ser), T (Thr), V (Val), W (Trp), and Y (Tyr)).

According to certain embodiments, the immunoglobulin binding ligand has the following structure II (written from amino terminus to carboxy terminus):

$$Z\text{-}X^1\text{-}X^2\text{-}X^3\text{-}X^4\text{-}X^5\text{-}X^6\text{-}X^7\text{-}W\text{-}F\text{-}U \quad \text{(Structure II)}$$

where $X^1$ and $X^2$ independent from each other are present or not, and wherein $X^1$, $X^2$, $X^3$, $X^4$, $X^5$, $X^6$, $X^7$, Z and U are as defined above.

According to certain embodiments, the immunoglobulin binding ligand has the following structure III (written from amino terminus to carboxy terminus)

$$Z\text{-}R^1\text{-}R^2\text{-}R^3\text{-}R^4\text{-}R^5\text{-}R^6\text{-}R^7\text{-}R^8\text{-}R^9\text{-}U \quad \text{(Structure III)}$$

wherein: $R^1$ may or may not be present, but if it is present is G; $R^2$ may or may not be present, but if it is present is S, T, C, N or K; $R^3$ is Y, W or F; $R^4$ is Y, W or F; $R^5$ is Y, W or F; $R^6$ is A, D, N, E or Q; $R^7$ is V, A, K, C, I, L or M; $R^8$ is W, Y or F; $R^9$ is F, W or Y; U is a C-terminal carboxyl group or a hydrogen atom replacing the C-terminal carboxyl group, or a linker or a capping group bound either to the C-terminal carbonyl group or directly to the alpha C-atom of C-terminal residue; and Z is an N-terminal amino group or a hydrogen atom replacing the N-terminal amino group, or a linker or a capping group bound either to the N-terminal amino group or directly to the alpha C-atom of the N-terminal residue.

The specific examples of the ligand of this invention include, but are not limited to, those listed in Table 2.

TABLE

Amino acid sequences of the preferred ligands.

| SEQ ID NO | Amino acid sequence |
|---|---|
| 1 | AGNGSYWYQVWF |
| 2 | GSYWYQVWF |
| 3 | SYWYQVWF |
| 4 | GYWYQVWF |
| 5 | YWYQVWF |
| 6 | GSYWYAVWF |
| 7 | SYWYAVWF |
| 8 | GYWYAVWF |
| 9 | YWYAVWF |
| 10 | GSYWYQAWF |
| 11 | SYWYQAWF |
| 12 | GYWYQAWF |
| 13 | YWYQAWF |
| 14 | GNYWYQVWF |
| 15 | NYWYQVWF |
| 16 | GTYWYQVWF |
| 17 | TYWYQVWF |
| 18 | GKYWYQVWF |
| 19 | KYWYQVWF |
| 20 | GCYWYQVWF |
| 21 | CYWYQVWF |
| 22 | GSYWYQKWF |
| 23 | SYWYQKWF |
| 24 | GYWYQKWF |
| 25 | YWYQKWF |
| 26 | GSYWYDVWF |
| 27 | SYWYDVWF |
| 28 | GYWYDVWF |
| 29 | YWYDVWF |
| 30 | GSYWYEVWF |
| 31 | SYWYEVWF |
| 32 | GYWYEVWF |
| 33 | YWYEVWF |
| 34 | GSYWYKVWF |
| 35 | SYWYKVWF |
| 36 | GYWYKVWF |
| 37 | YWYKVWF |
| 38 | GSYWYAAWF |
| 39 | GSYWYAKWF |
| 40 | GSYWYDAWF |
| 41 | GSYWYDKWF |
| 42 | GSYWYEAWF |
| 43 | GSYWYEKWF |
| 44 | GSYWYKAWF |
| 45 | GSYWYKKWF |
| 46 | SYWYAAWF |
| 47 | SYWYAKWF |
| 48 | SYWYDAWF |
| 49 | SYWYDKWF |
| 50 | SYWYEAWF |
| 51 | SYWYEKWF |
| 52 | SYWYKAWF |
| 53 | SYWYKKWF |
| 54 | GTYWYAVWF |

TABLE -continued

Amino acid sequences of the preferred ligands.

| SEQ ID NO | Amino acid sequence |
|---|---|
| 55 | GTYWYQAWF |
| 56 | GTYWYAAWF |
| 57 | GTYWYAKWF |
| 58 | GTYWYDVWF |
| 59 | GTYWYDAWF |
| 60 | GTYWYDKWF |
| 61 | GTYWYEVWF |
| 62 | GTYWYEAWF |
| 63 | GTYWYEKWF |
| 64 | GTYWYKVWF |
| 65 | GTYWYKAWF |
| 66 | GTYWYKKWF |
| 67 | GTYWYQKWF |
| 68 | TYWYAVWF |
| 69 | TYWYQAWF |
| 70 | TYWYAAWF |
| 71 | TYWYAKWF |
| 72 | TYWYDVWF |
| 73 | TYWYDAWF |
| 74 | TYWYDKWF |
| 75 | TYWYEVWF |
| 76 | TYWYEAWF |
| 77 | TYWYEKWF |
| 78 | TYWYKVWF |
| 79 | TYWYKAWF |
| 80 | TYWYKKWF |
| 81 | TYWYQKWF |
| 82 | GNYWYAVWF |
| 83 | GNYWYQAWF |
| 84 | GNYWYAAWF |
| 85 | GNYWYAKWF |
| 86 | GNYWYDVWF |
| 87 | GNYWYDAWF |
| 88 | GNYWYDKWF |
| 89 | GNYWYEVWF |
| 90 | GNYWYEAWF |

TABLE -continued

Amino acid sequences of the preferred ligands.

| SEQ ID NO | Amino acid sequence |
|---|---|
| 91 | GNYWYEKWF |
| 92 | GNYWYKVWF |
| 93 | GNYWYKAWF |
| 94 | GNYWYKKWF |
| 95 | GNYWYQKWF |
| 96 | NYWYAVWF |
| 97 | NYWYQAWF |
| 98 | NYWYAAWF |
| 99 | NYWYAKWF |
| 100 | NYWYDVWF |
| 101 | NYWYDAWF |
| 102 | NYWYDKWF |
| 103 | NYWYEVWF |
| 104 | NYWYEAWF |
| 105 | NYWYEKWF |
| 106 | NYWYKVWF |
| 107 | NYWYKAWF |
| 108 | NYWYKKWF |
| 109 | NYWYQKWF |
| 110 | YWYAAWF |
| 111 | YWYAKWF |
| 112 | YWYDAWF |
| 113 | YWYDKWF |
| 114 | YWYEAWF |
| 115 | YWYEKWF |
| 116 | YWYKAWF |
| 117 | YWYKKWF |
| 118 | GCYWYAVWF |
| 119 | GCYWYQAWF |
| 120 | GCYWYAAWF |
| 121 | GCYWYAKWF |
| 122 | GCYWYDVWF |
| 123 | GCYWYDAWF |
| 124 | GCYWYDKWF |
| 125 | GCYWYEVWF |
| 126 | GCYWYEAWF |

TABLE -continued

Amino acid sequences of the preferred ligands.

| SEQ ID NO | Amino acid sequence |
|---|---|
| 127 | GCYWYEKWF |
| 128 | GCYWYKVWF |
| 129 | GCYWYKAWF |
| 130 | GCYWYKKWF |
| 131 | GCYWYQKWF |
| 132 | CYWYAVWF |
| 133 | CYWYQAWF |
| 134 | CYWYAAWF |
| 135 | CYWYAKWF |
| 136 | CYWYDVWF |
| 137 | CYWYDAWF |
| 138 | CYWYDKWF |
| 139 | CYWYEVWF |
| 140 | CYWYEAWF |
| 141 | CYWYEKWF |
| 142 | CYWYKVWF |
| 143 | CYWYKAWF |
| 144 | CYWYKKWF |
| 145 | CYWYQKWF |
| 146 | GKYWYAVWF |
| 147 | GKYWYQAWF |
| 148 | GKYWYAAWF |
| 149 | GKYWYAKWF |
| 150 | GKYWYDVWF |
| 151 | GKYWYDAWF |
| 152 | GKYWYDKWF |
| 153 | GKYWYEVWF |
| 154 | GKYWYEAWF |
| 155 | GKYWYEKWF |
| 156 | GKYWYKVWF |
| 157 | GKYWYKAWF |
| 158 | GKYWYKKWF |
| 159 | GKYWYQKWF |
| 160 | KYWYAVWF |
| 161 | KYWYQAWF |
| 162 | KYWYAAWF |

TABLE -continued

Amino acid sequences of the preferred ligands.

| SEQ ID NO | Amino acid sequence |
|---|---|
| 163 | KYWYAKWF |
| 164 | KYWYDVWF |
| 165 | KYWYDAWF |
| 166 | KYWYDKWF |
| 167 | KYWYEVWF |
| 168 | KYWYEAWF |
| 169 | KYWYEKWF |
| 170 | KYWYKVWF |
| 171 | KYWYKAWF |
| 172 | KYWYKKWF |
| 173 | KYWYQKWF |
| 174 | HYTTYKSYISIF |
| 175 | EMRVYTSHLSYH |
| 176 | VSTVSYSFLQRS |
| 177 | SGSYAPPMSRYS |
| 178 | WTKTSSISFKTP |
| 179 | SWYKSSISSKQF |

An immunoglobulin binding ligand of the present invention may comprise an amino acid sequence having at least 60%, such as at least 70%, sequence identity with any one of the amino acid sequences SEQ ID NO: 1 to SEQ ID NO: 179.

An immunoglobulin binding ligand of the present invention may comprise an amino acid sequence having at least 80%, such as at least 90%, sequence identity with any one of the amino acid sequences SEQ ID NO: 1 to SEQ ID NO: 179.

An immunoglobulin binding ligand of the present invention may comprise an amino acid sequence having at least 90%, such as at least 95%, sequence identity with any one of the amino acid sequences SEQ ID NO: 1 to SEQ ID NO: 179.

An immunoglobulin binding ligand of the present invention may comprise an amino acid sequence having at least 60%, such as at least 70%, sequence identity with any one of the amino acid sequences SEQ ID NO: 2 to SEQ ID NO: 173.

An immunoglobulin binding ligand of the present invention may comprise an amino acid sequence having at least 80%, such as at least 90%, sequence identity with any one of the amino acid sequences SEQ ID NO: 2 to SEQ ID NO: 173.

An immunoglobulin binding ligand of the present invention may comprise an amino acid sequence having at least 90%, such as at least 95%, sequence identity with any one of the amino acid sequences SEQ ID NO: 2 to SEQ ID NO: 173.

An immunoglobulin binding ligand of the present invention may be a variant of a ligand comprising any one of the amino acid sequences SEQ ID NO: 1 to SEQ ID NO: 179, wherein one or more (such as one, two, three, four or five) amino acids in the reference sequence SEQ ID NO: 1 to SEQ ID NO: 179 are substituted by conservative substitutions.

An immunoglobulin binding ligand of the present invention may be a variant of a ligand comprising any one of the amino acid sequences SEQ ID NO: 2 to SEQ ID NO: 173, wherein one or more (such as one, two, three, four or five) amino acids in the reference sequence SEQ ID NO: 2 to SEQ ID NO: 173 are substituted by conservative substitutions.

An immunoglobulin binding ligand of the present invention may be a variant of a ligand comprising any one of the amino acid sequences SEQ ID NO: 1 to SEQ ID NO: 179, wherein one to five (such as one to three) amino acids in the reference sequence SEQ ID NO: 1 to SEQ ID NO: 179 are substituted by conservative substitutions.

An immunoglobulin binding ligand of the present invention may be a variant of a ligand comprising any one of the amino acid sequences SEQ ID NO: 2 to SEQ ID NO: 173, wherein one to five (such as one to three) amino acids in the reference sequence SEQ ID NO: 2 to SEQ ID NO: 173 are substituted by conservative substitutions.

According to certain embodiments, the following compound is excluded: H-D-Phe-L-Phe-L-Tyr-D-Trp-L-Lys-L-Val-L-Phe-D-Phe-NH$_2$. (SEQ ID NO:218).

The ligand of the present invention is capable of specifically binding to the Fc fragment of immunoglobulin and particularly to the IgG Fc fragment.

The present invention provides methods for detecting, purifying, or removing, separating, labelling, non-covalent cross-linking or capturing the Fc fragment moiety by the use of a ligand of the present invention. The ligand according to the invention may be useful in any method relying on affinity for Fc fragment of immunoglobulins. Thus, the ligand may be used as a detection reagent, a capture reagent or a separation reagent in such methods. Methods that employ the ligand according to the invention in vitro may be performed in different formats, such as microtiter plate, latex or paramagnetic beads, on biosensor surface or suitable solid support for chromatography.

Mutagenesis studies have been carried out on peptide ligand towards various goals, with substitutions typically made to alanine (referred to as alanine scanning) or guided by sequence homology substitutions. The substitutions affect binding to Fc fragment. Peptide ligand variants with selectively enhanced binding to Fc region have been shown to provide enhanced potency and specificity in functional assays. Mutagenesis studies have mapped the crucial amino acids in peptide ligands for binding a site on Fc fragment. Mutagenesis aimed at enhancing the affinity of the peptide to the antibody Fc region and simplifying its structure.

The present invention may be combined with other amino acid modifications of the ligand and/or amino acid additions to the ligand. The modifications/additions according to the invention may be performed in order to tailor the ligand to the specific use intended, without departing from the scope of the present invention. Such modifications and additions may provide altered or optimized interaction with Fc fragment (described in more detail below in Examples), and may comprise additional amino acids in the same peptide chain, or labels and/or therapeutic agents that are chemically conjugated or otherwise bound to the ligand according to the invention. Furthermore, the invention also encompasses fragments of the ligand that retain the capability of binding to Fc fragment of immunoglobulins.

In the present invention a labelling substance can be attached to the ligand. The ligand to which a labelling substance has been attached can be easily detected with high sensitivity. Examples of labelling substances include, but are not limited to, haptenic group, biotin, fluorescent proteins, fluorescent dyes, chemoluminescent dyes, enzymes and radioisotopes. Specific examples of the labelling substance include biotin and fluorescein. Methods for labelling ligand and protein using these labelling substances are well-known to persons skilled in the art. For example, biotin can also be attached to the ligand of the present invention via biotinylation using a commercially available reagent such as Sulfo-NHS-LC-Biotin (Pierce). A labelling substance may also be attached to the ligand of the present invention via a linker. This linker can be any substance capable of constituting a link between a ligand and a labelling substance, such as a peptide, fatty acid, a fatty acid ester and derivates of polyethylene glycol. Such linker may be inserted between the Fc-binding ligand and the labelling substance as a spacer to avoid steric hinderence, or as a cleavable link containing either a protease recognition site or chemically degradable bonds such hydrazone bonds.

The invention encompasses multimers of the ligand with affinity for the Fc fragment of immunoglobulins with the goal of obtaining stronger binding than is possible with only one ligand according to the invention. In this case, the provision of a multimer, such as dimer, trimer, tetramer, pentamer, or a higher order dendrimer may provide the necessary avidity effects. The multimer may consist of a suitable number of ligands according to the invention. This multimers are formed in such way, that they may have the same structure (representing homomultimers), but it is equally possible that they have different structure (representing heteromultimers). The linked ligands units in multimers according to the invention may be connected by covalent coupling using known organic chemistry. If ligand has a peptide structure the multimer may be expressed as one or more recombinant fusion peptides, or joined in any other fashion, directly or mediated by linker comprising a number of amino acids. In addition, biotinylated ligand units may be linked into multimers also by non-covalent complexes with streptavidin, neutravidin or avidin.

3. Solid Supports and Ligand Coupling to Solid Support

Any suitable solid support may be used in the present invention. Solid supports include inorganic materials, organic materials, and combinations thereof. Examples of suitable solid support materials include membranes, semipermeable membranes, capillaries, microarrays, multiple-well plates comprised of alumina, alumina supported polymers, polysaccharides including agarose, dextran, cellulose, chitosan, and polyacrylamide, polyacrylate, polystyrene, polyvinyl alcohol, glass, silica, silicon, zirconia, magnetite, semiconductors and combinations thereof. The solid support material may be in the form of beads, which are generally spherical. Alternatively, the support may be particulate or divided form having other regular or irregular shapes, or it may be in the form of an integrated material such as a sheet, monolithic chromatographic stationary phase or a surface of a plate, tube, or well. Preferred solid support materials are those having minimal non-specific binding properties and that are physically and chemically resistant to the conditions used in the purification process employed in this invention such as changes in pH and ionic strength.

The solid support used in the present invention is preferably a polymer of acrylate or styrene. Examples of acrylate polymers include, but are not limited to, polymethacrylate, polyhydroxy methacrylate, polymethyl methacrylate, polyacrylamide, polyacrylonitrile and other acrylate derivatives. More preferably, the solid support is a methacrylate polymer. Most preferably, the methacrylate polymer is hydroxylated polymethacrylate amino resin with a bead size of 1000 Å and a particle size of 5-300 µm. Examples of styrene polymers include, but are not limited to, unmodified and modified (e.g., irradiated or functionalized) polystyrene surfaces.

Ligands may be bound to solid support resin either directly or indirectly. When bound directly, the ligand is coupled to the solid support material by formation of covalent chemical bonds between particular functional groups on the ligand (e.g., primary amines, sulfhydryls, carboxylic acids, hydroxyls, and aldehydes) and reactive groups on the support. A variety of activating compounds and schemes for directly bonding ligands to solid phase supports are known in the art. The procedures by which such activating steps are carried out are well known to those skilled in the art.

Ligands of this invention may or may not have linking or spacer groups bonded to the N- or C-termini which when present may be used to bind the ligand to the solid support indirectly. The coupling of ligands to solid supports via spacer groups is a process well known in the art. When present, the linking group may be a polymer or a monomer. A linking group may be a chain of 1-20 amino acids in length, with linkers of 1 to 10 amino acids in length being most preferred. Other examples of linking groups include, but are not limited to, polyethylene glycol, polypropylene glycol, polyesters, polypeptides, polyethers, polysaccharides, glycidoxyalkyl, alkoxyalkyl, alkyl, glycidoxypropyl, ethyl, propyl, phenyl and methacryl.

4. Other Methods of Use

The ligands of the present invention may be fused or conjugated to one or more other molecules or peptides or proteins. Conjugate and fusion partners may be any molecule, including small molecule chemical compounds and peptides. Possible conjugate partners include but are not limited to cytokines, cytotoxic agents, toxins, chelator groups, radioisotopes, chemotherapeutic agent, anti-angiogenic agents, tyrosine kinase inhibitors, and other therapeutically active agents.

In some embodiments, conjugate partners may be thought of as payloads, that is to say that the goal of a conjugate is targeted delivery of the conjugate partner to a targeted cell, for example a cancer cell or immune cell, by the ligand of this invention via antibody that serves as the active targeting moiety. Thus, for example, the conjugation of a toxin to an antibody or Fc fusion targets the delivery of said toxin to cells expressing the target antigen. As will be appreciated by one skilled in the art, in reality the concepts and definitions of fusion and conjugate are overlapping. The designation of a ligand as a fusion or conjugate is not meant to constrain it to any particular embodiment of the present invention.

Fusion and conjugate partners may be linked to any region of a ligand of the present invention, including the N- or C-termini, or to some residue in-between the termini. In a preferred embodiment, a fusion or conjugate partner is linked to the N- or C-terminus of the ligand, most preferably the C-terminus. A variety of linkers may find use in the present invention to covalently link ligands to a fusion or conjugate partner. In a preferred embodiment, modifications are made to improve biophysical properties of the ligands of the present invention, including but not limited to stability and solubility. Modifications can include, for example, substitutions that provide more favourable properties of the ligand such as to provide greater stability, or substitution of exposed nonpolar amino acids with polar amino acids to increase solubility. A number of optimization goals and methods may find use for introduction of additional modifications to further optimize the ligands of the present invention.

In further embodiments, the ligands of the present invention comprise modifications that remove proteolytic degradation sites. These may include, for example, protease cleavage sites that reduce production yields, as well as protease cleavage sites that make the administered protein prone to degradation in vivo. In a preferred embodiment, additional modifications are made to remove covalent degradation sites such as sites of deamidation (i.e. deamidation of glutaminyl and asparaginyl residues to the corresponding glutamyl and aspartyl residues), oxidation, and proteolytic degradation sites. Deamidation sites that are particularly useful to remove are those that have enhanced propensity for deamidation, including, but not limited to asparaginyl and glutamyl residues followed by glycines (NG and QG motifs, respectively). Other covalent modifications, that can either be introduced or removed, include hydroxylation of proline and lysine, phosphorylation of hydroxyl groups of seryl or threonyl residues, methylation of the amino groups of lysine, arginine, and histidine side chains, acetylation of the N-terminal amine, and amidation of any C-terminal carboxyl group.

F. EXAMPLES

Examples are provided below to illustrate the present innovation. These examples are not meant to constrain the present invention and the technical scope of the present invention is not limited to this examples. Rather, the provided methods are meant to illustrate generally the binding of present invention to Fc fragment.

Example 1: Library Biopanning Against Human Fc Fragment and Selection of Peptide Ligands with Affinity for Fc fragment of IgG Three different phage display libraries were subjected to separate panning processes according to the protocol known to one skilled in the art. Various Fc-binding peptides were selected by targeting biotin-conjugated human Fc fragment prepared by random biotinylation of amine residues using EZ-Link™ Sulfo-NHS-SS-Biotin (Thermo Fisher Scientific, Rockford, IL, USA). After three rounds of affinity selection, individual clones were picked for phage Enzyme Linked Immuno-Sorbent Assay (ELISA) in order to evaluate their Fc fragment binding ability.

Wells of a 96-well microplate (Nunc, Maxisorp) were either coated with human Fc fragment solution or streptavidin as negative control. The wells were blocked with BSA and contacted with amplified population of each individual clone. Bound phages were detected by the addition of horseradish peroxidase (HRP)-conjugated anti-M13 monoclonal antibodies using the chromogenic substrate (3,3',5,5'-tetramethylbenzidine (TMB)) solution, and absorbance at 450 nm was measured. Results of phage ELISA for selected phage clones are shown in FIG. 1. The inserts encoding displayed peptides were sequenced.

Example 2: The Prediction of Binding Site on Fc Fragment

To locate the binding site of the strongest binding phage clone displaying the peptide with amino acid sequence identical to SEQ ID NO: 1 on the human IgG Fc fragment, a competitive phage fluorescence-linked immunosorbent assay (FLISA) was carried out using Staphylococcal protein A (SpA; cell wall constituent protein derived from Staphylococcal *aureus*). SpA is known to interact specifically with the region at the $C_H2$-$C_H3$ interface of immunoglobulins. Wells of the black Nunc MaxiSorp microtiter plate were either coated with human IgG Fc fragment or left uncoated (controls). Wells were blocked with BSA and contacted with purified fluorescein-labelled phage clone (the labelling procedure was adapted from the instructions of FITC manufacturer, Sigma-Aldrich). Phage was allowed to compete for the Fc binding with SpA in concentrations 1 µM, 100 nM or 10 nM. After 1 h-incubation at room temperature, the content was discarded and wells were washed with 0.1% PBST and finally filled with PBS. Fluorescence intensities in individual wells were measured at 510 nm upon excitation at 485 nm. The experiment was performed in triplicate.

As shown in FIG. 2, the higher the concentration of SpA added, the more effectively is binding of the phage clone to human IgG Fc fragment inhibited. The results indicate that the binding sites of SpA and the peptide with amino acid sequence identical to SEQ ID NO: 1 on Fc fragment at least partially overlap. Since SpA is known to bind to the junction of $C_H2$-$C_H3$ domains of human Fc fragment, it is considered that the peptide's binding site is located at the $C_H2$-$C_H3$ interface.

Example 3: Identification of the Minimal Fc-Binding Motif

To evaluate the minimal sequence requirements for binding the Fc region, the series of N- and C-terminally truncated peptides based on the parent peptide SEQ ID NO: 1 were designed (see FIG. 3) and displayed on phage surface. All mutant phage-displayed peptides were evaluated by phage ELISA for binding the Fc region relative to the parent clone displaying the peptide SEQ ID NO: 1 as described above. The experiment was performed in triplicate. The results are presented in FIG. 3.

In order to investigate the contribution of individual amino acid residues of the truncated peptide SEQ ID NO: 2 to the Fc binding, alanine scanning strategy was carried out. Individual alanine mutant-encoding DNA fragments were cloned into the M13KE phage vector (see FIG. 4). Phage-displayed peptides were evaluated by phage ELISA and Fc-binding was directly compared with Fc-binding of the parent clone displaying the peptide SEQ ID NO: 1 in triplicates. The results are shown in FIG. 4. The majority of substitutions reduce or completely eliminate interaction with the Fc fragment. However, we determined specific positions where alanine substitutions were well tolerated in terms of preserving binding activity. Moreover, in some cases residues other than alanine on such non-critical positions further improved binding affinity and specificity of peptides as demonstrated in functional assays (e.g., FIG. 7). There is currently no three-dimensional structure available for the complex comprising described peptides and Fc fragment or antibody molecule; however, mutagenesis studies have mapped the crucial amino acids in peptides for binding the Fc fragment.

Example 4: Evaluation of Binding Specificity to Different IgGs

The binding activity of phage clone displaying the minimized peptide SEQ ID NO: 2, was further evaluated by phage ELISA (as described above) using different subclasses of native human IgGs and different therapeutic monoclonal antibodies. BSA, avidin and SA were used as targets in negative control wells. The results are shown in FIG. 5. Phage clone displaying the peptide SEQ ID NO: 2 strongly bound to all of the human IgG subclasses and all of the tested therapeutic monoclonal antibodies. On the other hand, no significant binding to negative controls was observed.

Example 5: Binding Activity of Synthetic Peptides to Different IgGs

Based on the amino acid sequences of phage displayed peptides with high binding activity we designed synthetic peptides. Synthetic peptide SEQ ID NO: 2 with C-terminal linker SEQ ID 181 biotinylated at ε-amino group of residue K ($NH_2$-GSYWYQVWFGGGSR(K-ε-biotin)-$CONH_2$) was prepared. Further, additional peptides SEQ ID NO: 30 and SEQ ID NO: 26 with biotinylated C-terminal linkers SEQ ID NO: 181 were designed and synthesized in which "Q" (Gln) at position 6 of the parental peptide SEQ ID 2 was substituted with "E" (Glu) and "D" (Asp), respectively.

The binding activity of the described biotinylated synthetic peptides to different immunoglobulins was evaluated using an assay akin to ELISA. Wells were coated with the different subclasses of human IgGs or human intravenous immunoglobulins. All the wells were blocked with BSA. A biotinylated synthetic peptide and horseradish peroxidase (HRP)-conjugated streptavidin (SA-HRP) were mixed in advance at molar ratio of 4:1 to formulate tetrameric (peptide)$_4$ SA-HRP complexes and then the mixtures were added to individual wells. After washing, the (peptide)$_4$ SA-HRP complexes were detected with TMB solution. The results are shown in FIG. 8. All three designed biotinylated synthetic peptides (SEQ ID NOs: 2, 30 and 26) specifically bound to human IgGs in a manner similar to the corresponding phage clones as described above in Example 4 (FIG. 5). The Q6E and especially Q6D substitutions significantly increased binding compared with the parental peptide SEQ ID NO: 2. All synthetic peptides exhibited strong binding activity to each human IgG subclass similar to their corresponding phage clones (not shown). The above results demonstrate that the synthetic peptides comprised of the peptide sequences identified in Example 1 by biopanning approach or analogous sequences thereof containing the described common motifs retain binding affinity and specificity for IgG antibodies (particularly Fc region of antibody) even when not expressed on the surface of bacteriophage capsid.

Additionally, the binding activity of the synthetic peptide SEQ ID NO: 2 to immunoglobulins of different animal species (mouse, rabbit, donkey, and sheep) was evaluated by an assay akin to ELISA essentially as described above. Peptides SEQ ID NO: 184 and SEQ ID NO: 185 represent two control biotin-labelled synthetic peptides with unrelated amino acids sequences. The results are shown in FIG. 6. Synthetic peptide SEQ ID NO: 2 specifically bound to IgGs of different animal species.

Moreover, the binding activity of the biotinylated synthetic peptides to bind selected therapeutic monoclonal IgGs (infliximab (chimeric $IgG_1$) and nivolumab (human $IgG_4$)) was determined by ELISA essentially as described above. SA-HRP conjugate alone (i.e., not coupled to peptides) was used as negative control. The results are shown in FIG. 7. Peptide ligands exhibited strong binding to both monoclonal therapeutic IgGs and human intravenous immunoglobulins.

Example 6: Kinetic Analysis of Interaction Between the Ligand of the Present Invention and Human Fc Fragment Interaction between the synthetic biotinylated peptide ligand with amino acid sequence identical to SEQ ID NO: 2 and human Fc fragment was analyzed by surface plasmon resonance (SPR) using BIAcoreX100 (BIAcore) at 25° C. Biotinylated synthetic peptide of the present invention was immobilized to the matrix indirectly through streptavidin. Streptavidin (SA) was immobilized to the surface of CM-5 chip through random amine coupling according to the manufacturer's recommendations to achieve a stable response corresponding to approximately 4000 resonance units. The first cell surface was prior activated and deactivated and used as a reference cell during injections. After successful covalent immobilization of SA to dextran matrix via amino groups, a 120 nM solution (pH 5) of biotinylated synthetic peptide SEQ ID NO: 2 was injected over a sensor chip SA to immobilize the peptide onto the chip. The amount of immobilized peptide was adjusted to the stable response corresponding to approximately 200 RU. Subsequently, solutions of human Fc fragment (the analyte) of various concentrations (10 nM, 20 nM, 40 nM, 80 nM, and 160 nM) in running buffer (0.005% P20 in PBS) were injected at a flow rate of 10 µL/min at through flow cells in a manner known as single cycle. Binding reaction between human Fc fragment and the peptide was recorded. Thereafter, washing with running buffer was conducted and then dissociation reaction was observed. The surface was regenerated with injections of 0.5 mM NaOH. Binding parameters were derived after data processing using BIA evaluation Version 3.2 software.

Sensograms obtained by the SPR analysis described above are shown in FIG. 10. As shown, immobilized peptide SEQ ID NO: 2 exhibited binding to human Fc. The results are consistent with the evaluation of the binding by the above ELISA assay. In addition, the results indicate slow dissociation rate.

Example 7: Pull-Down Assay of Human Immunoglobulins Using the Peptide Ligand of the Present Invention as Affinity Ligands Selected peptides (SEQ ID NO: 2, SEQ ID NO: 30, and SEQ ID NO: 26) with biotin attached via epsilon-amino group of C-terminal amidated lysine in added linker SEQ ID NO: 181 were synthesized and coupled to streptavidin-coated paramagnetic beads. The same paramagnetic beads without addition of peptide and the same paramagnetic beads coupled with unrelated biotinylated peptide SEQ. ID 185 were used as negative controls. First, the Fc fragment of human antibodies (2 µg) was spiked into PBS and incubated with peptide-coated paramagnetic beads. The beads were then pelleted, washed with 0.1% PBST, and the bound material was eluted with acidic buffer (0.2 M glycine/HCl, pH 2.2). The low pH eluate was immediately neutralized with 1M Tris/HCl, pH 9.1. The eluates obtained from pull-down assay were analyzed by DotBlot assay and Western blotting using polyclonal goat anti-human IgG (H+L) HRP conjugate for detection (results not shown). Equivalent pull-down assay was carried out also from serum free DMEM growth medium spiked with human Fc fragment (2 µg) with peptide SEQ ID NO: 2 (FIG. 11). Additionally, the pull-down assay was also made from intact human sera. The presence of human IgGs in the eluate was confirmed by Coomassie blue staining (FIG. 13) and Western blot analysis (FIG. 12) using HRP-conjugated goat anti-human (H+L) antibodies (BioRad).

The results of pull-down assays are shown in FIG. 11-14. As shown, human IgG Fc fragment as well as native human IgGs were successfully isolated from spiked serum free DMEM growth medium and human serum using the paramagnetic beads coated with the ligands according to the invention. The synthetic peptide ligand SEQ ID NO: 26 exhibited trapping efficiency significantly higher than the parent peptide SEQ ID NO: 2. The human IgG levels in pull-down assay eluates from SEQ ID NO: 2-, SEQ ID NO: 30-, and SEQ ID NO: 26-coated beads correlated with IgG bindings of individual peptides in prior assays akin to ELISA (e.g., FIG. 8). The above results show that the peptides of the present invention selectively bind to human IgGs and that the antibodies can be effectively eluted from the matrix by lowering pH.

Example 8: Preparation of Affinity Chromatography Column Based on the Peptide as Present Invention Two representative peptides (SEQ ID NO: 2 and SEQ ID NO: 26) with binding affinity for the Fc fragment were selected for additional studies of their performance as affinity ligands in affinity chromatography. Separation of IgGs from different samples, including complex media and human sera, was carried out using the prepared columns with both peptides of this invention immobilized to the matrix.

Peptide was coupled to CNBr-activated agarose. Briefly, CNBr-activated sepharose was swollen in cold 1 mM HCl in several aliquots and added onto sintered glass filter column. The excess HCl was removed between successive additions. The gel was washed with distilled water and then with coupling buffer (0.1 M NaHCO$_3$, pH 8.3 containing 0.5 M NaCl). Synthetic peptide SEQ ID NO: 2 with C-terminal linker SEQ ID NO: 182 was dissolved in coupling buffer and added to the CNBr-activated sepharose. After 1 h of gentle shaking at room temperature, the excess peptide was washed away with coupling buffer. The unreacted CNBr groups were capped with 1 M ethanolamine, pH 8.0. The blocking solution was washed extensively with distilled water and the slurry was packed in a 1 mL cartridge and connected onto Äkta explorer T10 chromatography platform (GE Healthcare). The resin was washed with three cycles of alternating pH. Each cycle consisted of a wash with 0.1 M acetic acid/sodium acetate, pH 4.0 containing 0.5 M NaCl followed by a wash with 0.1 M Tris-HCl, pH 8.0 containing 0.5 M NaCl. The column was then washed with distilled water and equilibrated with binding buffer (PBS).

PBS spiked with human IgGs and BSA in a 1:1 ratio was injected onto the column at a flow rate 0.3 mL/mL. The column was the washed with PBS containing 1 M NaCl followed by elution of bound material with glycine hydrochloride buffer pH 2.5. Eluted fractions were neutralized with 1 M Tris buffer pH 9 immediately after collection and subsequently analysed by SDS-PAGE. Gel was stained with Coomassie. The results are shown in FIG. 15.

REFERENCES

1. Shukla A A, Thommes J. Recent advances in large-scale production of monoclonal antibodies and related proteins. Trends Biotechnol. 2010 May; 28(5):253-61.

2. Li F, Vijayasankaran N, Shen A Y, Kiss R, Amanullah A. Cell culture processes for monoclonal antibody production. MAbs. 2010 September-October; 2(5):466-79.
3. Birch J R, Racher A J. Antibody production. Adv Drug Deliv Rev. 2006 Aug. 7; 58(5-6):671-85.
4. Roque A C, Silva C S, Taipa M A. Affinity-based methodologies and ligands for antibody purification: advances and perspectives. J Chromatogr A. 2007 Aug. 10; 1160(1-2):44-55.
5. Sidorin E V, Solov'eva T F. IgG-binding proteins of bacteria. Biochemistry (Mosc). 2011 March; 76(3):295-308.
6. Jungbauer A. Continuous downstream processing of biopharmaceuticals. Trends Biotechnol. 2013 August; 31(8):479-92.
7. Hanke A T, Ottens M. Purifying biopharmaceuticals: knowledge-based chromatographic process development. Trends Biotechnol. 2014 April; 32(4):210-20.
8. Chon J H, Zarbis-Papastoitsis G. Advances in the production and downstream processing of antibodies. N Biotechnol. 2011 September; 28(5):458-63.
9. Labrou N E. Design and selection of ligands for affinity chromatography. J Chromatogr B Analyt Technol Biomed Life Sci. 2003 Jun. 25; 790(1-2):67-78.
10. Koguma I, Yamashita S, Sato S, Okuyama K, Katakura Y. Novel purification method of human immunoglobulin by using a thermo-responsive protein A. J Chromatogr A. 2013 Aug. 30; 1305:149-53.
11. Nilsson B, Moks T, Jansson B, Abrahmsen L, Elmblad A, Holmgren E, et al. A synthetic IgG-binding domain based on staphylococcal protein A. Protein Eng. 1987 February-March; 1(2):107-13.
12. Kruljec N, Bratkovič T. Alternative Affinity Ligands for Immunoglobulins. Bioconjug Chem. 2017 Aug. 16; 28(8):2009-30.
13. Li R, Dowd V, Stewart D J, Burton S J, Lowe C R. Design, synthesis, and application of a protein A mimetic. Nat Biotechnol. 1998 February; 16(2):190-5.
14. Yang H, Gurgel P V, Carbonell R G. Purification of human immunoglobulin G via Fc-specific small peptide ligand affinity chromatography. J Chromatogr A. 2009 Feb. 6; 1216(6):910-8.
15. DeLano W L, Ultsch M H, de Vos A M, Wells J A. Convergent solutions to binding at a protein-protein interface. Science. 2000 Feb. 18; 287(5456):1279-83.

The invention claimed is:

1. An immunoglobulin binding ligand consisting of any one of the amino acid sequences of SEQ ID NO:2 to SEQ ID NO:173.

2. An immunoglobulin binding ligand consisting of the following structure:

$X^1X^2X^3X^4X^5X^6X^7X^8X^9$

Wherein:

$X^1$ is G;
$X^2$ is S, T, C, N or K;
$X^3$ is W or F;
$X^4$ is W, Y or F;
$X^5$ is Y, W or F;
$X^6$ is A, D, E, N, Q or K;
$X^7$ is V, A, K, C, I, L or M;
$X^8$ is W, Y or F; and
$X^9$ is F, W or Y.

* * * * *